(12) United States Patent
Lozier et al.

(10) Patent No.: US 8,753,406 B2
(45) Date of Patent: *Jun. 17, 2014

(54) OSTEOCHONDRAL GRAFT DELIVERY DEVICE AND USES THEREOF

(71) Applicant: Zimmer, Inc., Warsaw, IN (US)

(72) Inventors: Antony J. Lozier, Warsaw, IN (US); Daniel P. Murphy, Claypool, IN (US)

(73) Assignee: Zimmer Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,157

(22) Filed: Apr. 2, 2013

(65) Prior Publication Data

US 2013/0231745 A1  Sep. 5, 2013

Related U.S. Application Data

(63) Continuation of application No. 12/873,049, filed on Aug. 31, 2010, now Pat. No. 8,435,305.

(51) Int. Cl.
*A61F 2/28* (2006.01)
(52) U.S. Cl.
USPC .......................................... 623/23.48; 606/99
(58) Field of Classification Search
CPC .... A61B 2/30723; A61B 2/46; A61B 2/4603; A61B 2/4614
USPC ............ 606/86 A, 86 B, 92–94, 99, 104, 107, 606/914–916; 623/23.48; 294/100; 401/93
See application file for complete search history.

(56) References Cited

U.S. PATENT DOCUMENTS

| | | | |
|---|---|---|---|
| 493,730 | A | 3/1893 | McKenzie |
| 1,405,720 | A | 2/1922 | Scott |
| 1,567,910 | A | 12/1925 | Franz et al. |

(Continued)

FOREIGN PATENT DOCUMENTS

| | | |
|---|---|---|
| AU | 4922296 A | 9/1996 |
| AU | 700349 | 1/1997 |

(Continued)

OTHER PUBLICATIONS

"U.S. Appl. No. 10/149,853, Non Final Office Action mailed Apr. 13, 2004", 7 pgs.

(Continued)

*Primary Examiner* — Todd Manahan
*Assistant Examiner* — Eric S Gibson
(74) *Attorney, Agent, or Firm* — Schwegman Lundberg & Woessner, P.A.

(57) ABSTRACT

A delivery device for an osteochondral graft comprising a tube, a plunger and a graft retention assembly is disclosed. The tube has a bore having an inside diameter and extends from a proximal end to a distal end. The inside diameter of the bore is sufficient to accept an osteochondral graft of a desired diameter. The tube has a set of apertures located adjacent the distal end of the tube. The plunger is slidably disposed within the bore of the tube. The graft retention assembly comprises a collar and a set of tabs. The graft retention assembly is attached to the tube such that the tabs are disposed within the apertures of the tube. The tabs are biased towards each other but are capable of being displaced away from each other to receive or release the osteochondral graft.

11 Claims, 4 Drawing Sheets

(56) References Cited

U.S. PATENT DOCUMENTS

| | | |
|---|---|---|
| 1,703,154 A | 2/1929 | Lanzkron |
| 1,984,839 A | 12/1934 | Murray |
| 2,573,462 A | 10/1951 | Earle |
| 3,564,947 A | 2/1971 | Maier |
| 3,564,948 A | 2/1971 | Pomernacki |
| 3,841,909 A | 10/1974 | Nonaka et al. |
| 3,848,601 A | 11/1974 | Ma |
| 3,875,595 A | 4/1975 | Froning |
| 3,949,743 A | 4/1976 | Shanbrom |
| 3,971,273 A | 7/1976 | Peters et al. |
| 4,010,737 A | 3/1977 | Vilaghy et al. |
| 4,069,216 A | 1/1978 | Shanbrom |
| 4,086,218 A | 4/1978 | Shanbrom et al. |
| 4,105,650 A | 8/1978 | Shanbrom et al. |
| 4,137,223 A | 1/1979 | Shanbrom et al. |
| 4,142,592 A | 3/1979 | Brusselmans |
| 4,186,448 A | 2/1980 | Brekke |
| 4,188,318 A | 2/1980 | Shanbrom |
| 4,189,425 A | 2/1980 | Shanbrom et al. |
| 4,250,892 A | 2/1981 | Dolhay et al. |
| 4,277,184 A | 7/1981 | Solomon |
| 4,294,753 A | 10/1981 | Urist |
| 4,305,871 A | 12/1981 | Shanbrom |
| 4,314,997 A | 2/1982 | Shanbrom |
| 4,315,919 A | 2/1982 | Shanbrom |
| 4,378,224 A | 3/1983 | Nimni et al. |
| 4,387,092 A | 6/1983 | Liautaud et al. |
| 4,412,985 A | 11/1983 | Shanbrom |
| 4,465,623 A | 8/1984 | Chanas et al. |
| 4,571,921 A | 2/1986 | Wolfson |
| 4,589,206 A | 5/1986 | Marcoux |
| 4,627,853 A | 12/1986 | Campbell et al. |
| 4,645,488 A | 2/1987 | Matukas |
| 4,706,659 A | 11/1987 | Matthews et al. |
| 4,932,973 A | 6/1990 | Gendler |
| 4,933,169 A | 6/1990 | Shanbrom |
| 4,950,256 A | 8/1990 | Luther et al. |
| 4,997,915 A | 3/1991 | Tan et al. |
| 5,002,583 A | 3/1991 | Pitaru et al. |
| 5,019,495 A | 5/1991 | Shanbrom |
| 5,067,964 A | 11/1991 | Richmond et al. |
| 5,112,354 A | 5/1992 | Sires |
| 5,115,704 A | 5/1992 | Hyman |
| 5,128,149 A | 7/1992 | Shanbrom |
| 5,128,150 A | 7/1992 | Shanbrom |
| 5,139,520 A | 8/1992 | Rosenberg |
| 5,152,763 A | 10/1992 | Johnson |
| 5,152,791 A | 10/1992 | Hakamatsuka et al. |
| 5,156,973 A | 10/1992 | Shanbrom |
| 5,160,313 A | 11/1992 | Carpenter et al. |
| 5,165,824 A | 11/1992 | Corcoran et al. |
| 5,184,926 A | 2/1993 | Hemmings |
| 5,186,945 A | 2/1993 | Shanbrom |
| 5,197,833 A | 3/1993 | Mayer et al. |
| 5,204,324 A | 4/1993 | Shanbrom |
| 5,207,681 A | 5/1993 | Ghadjar et al. |
| 5,211,661 A | 5/1993 | Shinjou et al. |
| 5,259,971 A | 11/1993 | Smith Morse et al. |
| 5,320,115 A | 6/1994 | Kenna |
| 5,320,626 A | 6/1994 | Schmieding |
| 5,328,722 A | 7/1994 | Ghanayem et al. |
| 5,333,626 A | 8/1994 | Morse et al. |
| 5,341,816 A | 8/1994 | Allen |
| 5,345,927 A | 9/1994 | Bonutti |
| 5,360,605 A | 11/1994 | Shanbrom |
| 5,362,166 A | 11/1994 | Yamamoto et al. |
| 5,368,051 A | 11/1994 | Dunn et al. |
| 5,370,692 A | 12/1994 | Fink et al. |
| 5,370,869 A | 12/1994 | Shanbrom |
| 5,374,539 A | 12/1994 | Nimni et al. |
| 5,423,823 A | 6/1995 | Schmieding |
| 5,425,490 A | 6/1995 | Goble et al. |
| 5,443,468 A | 8/1995 | Johnson |
| 5,496,326 A | 3/1996 | Johnson |
| 5,513,662 A | 5/1996 | Morse et al. |
| 5,545,401 A | 8/1996 | Shanbrom |
| 5,556,379 A | 9/1996 | Wolfinbarger |
| 5,575,798 A | 11/1996 | Koutrouvelis |
| 5,587,912 A | 12/1996 | Andersson et al. |
| 5,589,072 A | 12/1996 | Shanbrom |
| 5,591,234 A | 1/1997 | Kirsch |
| 5,603,716 A | 2/1997 | Morgan et al. |
| 5,607,474 A | 3/1997 | Athanasiou et al. |
| 5,609,864 A | 3/1997 | Shanbrom |
| 5,613,982 A | 3/1997 | Goldstein |
| 5,632,745 A | 5/1997 | Schwartz |
| 5,632,747 A | 5/1997 | Scarborough et al. |
| 5,632,778 A | 5/1997 | Goldstein |
| 5,697,932 A | 12/1997 | Smith et al. |
| 5,716,413 A | 2/1998 | Walter |
| 5,718,707 A | 2/1998 | Mikhail |
| 5,741,685 A | 4/1998 | Vacanti |
| 5,741,782 A | 4/1998 | Brockbank et al. |
| 5,769,899 A | 6/1998 | Schwartz et al. |
| 5,770,705 A | 6/1998 | Shanbrom |
| 5,771,310 A | 6/1998 | Vannah |
| 5,782,835 A | 7/1998 | Hart et al. |
| 5,782,915 A | 7/1998 | Stone |
| 5,785,522 A | 7/1998 | Bergstrom et al. |
| 5,788,713 A | 8/1998 | Dubach et al. |
| 5,797,871 A | 8/1998 | Wolfinbarger, Jr. |
| 5,800,537 A | 9/1998 | Bell |
| 5,810,887 A | 9/1998 | Accorti, Jr. et al. |
| 5,811,471 A | 9/1998 | Shanbrom |
| 5,814,225 A | 9/1998 | Shanbrom |
| 5,817,153 A | 10/1998 | Pendl et al. |
| 5,820,581 A | 10/1998 | Wolfinbarger, Jr. |
| 5,843,182 A | 12/1998 | Goldstein |
| 5,853,746 A | 12/1998 | Hunziker |
| 5,854,397 A | 12/1998 | Mechanic |
| 5,858,641 A | 1/1999 | Shanbrom |
| 5,860,946 A | 1/1999 | Hofstatter |
| 5,865,803 A | 2/1999 | Major |
| 5,865,849 A | 2/1999 | Stone |
| 5,876,452 A | 3/1999 | Athanasiou et al. |
| 5,881,733 A | 3/1999 | Stone |
| 5,885,293 A | 3/1999 | Mcdevitt et al. |
| 5,888,061 A | 3/1999 | Reynolds |
| 5,899,860 A | 5/1999 | Pfeiffer et al. |
| 5,899,936 A | 5/1999 | Goldstein |
| 5,902,338 A | 5/1999 | Stone |
| 5,904,717 A | 5/1999 | Brekke et al. |
| 5,916,265 A | 6/1999 | Ju |
| 5,919,196 A | 7/1999 | Bobic et al. |
| 5,919,907 A | 7/1999 | Shanbrom |
| 5,921,987 A | 7/1999 | Stone |
| 5,922,027 A | 7/1999 | Stone |
| 5,944,755 A | 8/1999 | Stone |
| 5,976,104 A | 11/1999 | Wolfinbarger, Jr. |
| 5,977,432 A | 11/1999 | Wolfinbarger, Jr. et al. |
| 5,984,858 A | 11/1999 | Stone |
| 5,985,260 A | 11/1999 | Shanbrom |
| 5,993,451 A | 11/1999 | Burkhart |
| 5,993,844 A | 11/1999 | Abraham et al. |
| 6,013,853 A | 1/2000 | Athanasiou et al. |
| 6,017,348 A | 1/2000 | Hart et al. |
| 6,017,349 A | 1/2000 | Heller et al. |
| 6,019,765 A | 2/2000 | Thornhill et al. |
| 6,024,735 A | 2/2000 | Wolfinbarger, Jr. |
| 6,025,538 A | 2/2000 | Yaccarino, III |
| 6,027,743 A | 2/2000 | Khouri et al. |
| 6,036,738 A | 3/2000 | Chanbrom |
| 6,045,787 A | 4/2000 | Shanbrom |
| 6,046,379 A | 4/2000 | Stone et al. |
| 6,049,025 A | 4/2000 | Stone |
| 6,063,088 A | 5/2000 | Winslow |
| 6,063,210 A | 5/2000 | Chakrabarti et al. |
| 6,074,394 A | 6/2000 | Krause |
| 6,090,998 A | 7/2000 | Grooms et al. |
| 6,093,204 A | 7/2000 | Stone |
| 6,093,401 A | 7/2000 | Shanbrom |
| 6,096,216 A | 8/2000 | Shanbrom et al. |
| 6,110,178 A | 8/2000 | Zech et al. |
| 6,110,206 A | 8/2000 | Stone |

(56) References Cited

U.S. PATENT DOCUMENTS

| | | |
|---|---|---|
| 6,110,482 A | 8/2000 | Khouri et al. |
| 6,123,731 A | 9/2000 | Boyce et al. |
| 6,146,385 A | 11/2000 | Torrie et al. |
| 6,179,871 B1 | 1/2001 | Halpern |
| 6,183,764 B1 | 2/2001 | Shanbrom |
| 6,193,722 B1 | 2/2001 | Zech et al. |
| 6,210,440 B1 | 4/2001 | Stone et al. |
| 6,224,574 B1 | 5/2001 | Al-Labban |
| 6,231,608 B1 | 5/2001 | Stone |
| 6,235,035 B1 | 5/2001 | Boukhris |
| 6,242,247 B1 | 6/2001 | Reiser et al. |
| 6,251,143 B1 | 6/2001 | Schwartz et al. |
| 6,267,786 B1 | 7/2001 | Stone |
| 6,270,503 B1 | 8/2001 | Schmieding |
| 6,302,887 B1 | 10/2001 | Spranza et al. |
| 6,306,142 B1 | 10/2001 | Johanson et al. |
| 6,322,593 B1 | 11/2001 | Pathak |
| 6,350,732 B1 | 2/2002 | Moore et al. |
| 6,358,253 B1 | 3/2002 | Torrie et al. |
| 6,361,786 B1 | 3/2002 | Shanbrom |
| 6,375,658 B1 | 4/2002 | Hangody et al. |
| 6,382,204 B1 | 5/2002 | Jansen et al. |
| 6,383,732 B1 | 5/2002 | Stone |
| 6,395,011 B1 | 5/2002 | Johanson et al. |
| 6,402,783 B1 | 6/2002 | Stone |
| 6,440,141 B1 | 8/2002 | Philippon |
| 6,448,076 B2 | 9/2002 | Dennis et al. |
| 6,455,309 B2 | 9/2002 | Stone |
| 6,459,948 B1 | 10/2002 | Ateshian et al. |
| 6,468,314 B2 | 10/2002 | Schwartz et al. |
| 6,488,033 B1 | 12/2002 | Cerundolo |
| 6,511,511 B1 | 1/2003 | Slivka et al. |
| 6,520,964 B2 | 2/2003 | Tallarida et al. |
| 6,521,179 B1 | 2/2003 | Girardot et al. |
| 6,530,928 B1 | 3/2003 | Frei et al. |
| 6,541,518 B2 | 4/2003 | Shanbrom |
| 6,548,076 B2 | 4/2003 | Shanbrom |
| 6,569,200 B2 | 5/2003 | Wolfinbarger, Jr. et al. |
| 6,582,438 B2 | 6/2003 | DeMayo |
| 6,591,581 B2 | 7/2003 | Schmieding |
| 6,592,588 B2 | 7/2003 | Bobic et al. |
| 6,599,690 B1 | 7/2003 | Abraham et al. |
| 6,610,067 B2 | 8/2003 | Tallarida et al. |
| 6,610,316 B2 | 8/2003 | Shanbrom |
| 6,626,945 B2 | 9/2003 | Simon et al. |
| 6,626,950 B2 | 9/2003 | Brown et al. |
| 6,632,246 B1 | 10/2003 | Simon et al. |
| 6,652,592 B1 | 11/2003 | Grooms et al. |
| 6,656,195 B2 | 12/2003 | Peters et al. |
| 6,679,917 B2 | 1/2004 | Ek |
| 6,682,695 B2 | 1/2004 | Macphee et al. |
| 6,682,760 B1 | 1/2004 | Noff et al. |
| 6,689,161 B2 | 2/2004 | Chen et al. |
| 6,696,270 B2 | 2/2004 | Badylak et al. |
| 6,699,252 B2 | 3/2004 | Farr, II et al. |
| 6,727,224 B1 | 4/2004 | Zhang et al. |
| 6,734,018 B2 | 5/2004 | Wolfinbarger et al. |
| 6,743,435 B2 | 6/2004 | Devore et al. |
| 6,743,574 B1 | 6/2004 | Wolfinbarger, Jr. et al. |
| 6,758,865 B1 | 7/2004 | Stone et al. |
| 6,767,354 B2 | 7/2004 | Johanson et al. |
| 6,793,429 B2 | 9/2004 | Arrison |
| 6,793,676 B2 | 9/2004 | Plouhar et al. |
| 6,821,533 B2 | 11/2004 | Shanbrom |
| 6,837,907 B2 | 1/2005 | Wolfinbarger, Jr. et al. |
| 6,841,060 B2 | 1/2005 | Shanbrom |
| 6,852,114 B2 | 2/2005 | Cerundolo |
| 6,852,125 B2 | 2/2005 | Simon et al. |
| 6,855,169 B2 | 2/2005 | Boyer et al. |
| 6,858,042 B2 | 2/2005 | Nadler et al. |
| 6,863,905 B1 | 3/2005 | Shanbrom |
| 6,881,731 B1 | 4/2005 | Shanbrom |
| 6,884,245 B2 | 4/2005 | Spranza, III |
| 6,893,653 B2 | 5/2005 | Abraham et al. |
| 6,933,103 B1 | 8/2005 | Klein et al. |
| 6,972,041 B1 | 12/2005 | Stone |
| 6,988,015 B1 | 1/2006 | Schopf et al. |
| 6,998,418 B1 | 2/2006 | Sung et al. |
| 7,008,763 B2 | 3/2006 | Cheung |
| 7,029,479 B2 | 4/2006 | Tallarida et al. |
| 7,037,339 B2 | 5/2006 | Houfburg |
| 7,048,477 B2 | 5/2006 | Abrams |
| 7,060,022 B2 | 6/2006 | Chen et al. |
| 7,064,187 B2 | 6/2006 | Stone |
| 7,129,035 B2 | 10/2006 | Goldstein et al. |
| 7,160,305 B2 | 1/2007 | Schmieding |
| 7,175,979 B2 | 2/2007 | Luwel et al. |
| 7,217,294 B2 | 5/2007 | Kusanagi et al. |
| 7,264,634 B2 | 9/2007 | Schmieding |
| 7,291,149 B1 | 11/2007 | Michelson |
| 7,297,716 B2 | 11/2007 | Shanbrom |
| 7,323,445 B2 | 1/2008 | Zhang et al. |
| 7,371,260 B2 | 5/2008 | Malinin |
| 7,410,947 B2 | 8/2008 | Rueger et al. |
| 7,411,006 B2 | 8/2008 | Shanbrom |
| 7,416,371 B2 | 8/2008 | Scott et al. |
| 7,427,293 B2 | 9/2008 | Nycz et al. |
| RE40,570 E | 11/2008 | Carpentier et al. |
| 7,548,865 B2 | 6/2009 | Schmieding |
| 7,550,007 B2 | 6/2009 | Malinin |
| 7,563,266 B2 | 7/2009 | Camino et al. |
| 7,572,291 B2 | 8/2009 | Gil et al. |
| 7,591,820 B2 | 9/2009 | Schmieding et al. |
| 7,608,098 B1 | 10/2009 | Stone |
| 7,666,230 B2 | 2/2010 | Orban |
| 7,758,583 B2 | 7/2010 | Gil et al. |
| 7,758,643 B2 | 7/2010 | Stone et al. |
| 7,776,043 B2 | 8/2010 | Hycz et al. |
| 7,833,269 B2 | 11/2010 | Nycz et al. |
| 7,862,567 B2 | 1/2011 | Schmieding |
| 7,875,032 B2 | 1/2011 | Lyons |
| 7,879,040 B2 | 2/2011 | Bharadwaj |
| 7,887,546 B2 | 2/2011 | Gil |
| 7,905,904 B2 | 3/2011 | Stone et al. |
| 7,909,851 B2 | 3/2011 | Stone et al. |
| 7,909,873 B2 | 3/2011 | Tan-Malecki et al. |
| 7,914,539 B2 | 3/2011 | Stone et al. |
| 7,955,335 B2 | 6/2011 | Gil et al. |
| 7,955,336 B2 | 6/2011 | Gil et al. |
| 7,985,230 B2 | 7/2011 | Gil et al. |
| 7,997,174 B2 | 8/2011 | Gil et al. |
| 8,034,090 B2 | 10/2011 | Stone et al. |
| 8,048,079 B2 | 11/2011 | Iannarone |
| RE43,714 E | 10/2012 | Nadler et al. |
| 8,435,305 B2 * | 5/2013 | Lozier et al. ............ 623/23.48 |
| 2001/0000804 A1 | 5/2001 | Goldstein et al. |
| 2001/0051828 A1 | 12/2001 | Stone et al. |
| 2002/0013627 A1 | 1/2002 | Geistlich et al. |
| 2002/0026244 A1 | 2/2002 | Trieu |
| 2002/0082704 A1 | 6/2002 | Cerundolo |
| 2002/0087211 A1 | 7/2002 | Stone et al. |
| 2002/0102287 A1 | 8/2002 | Shanbrom |
| 2002/0117403 A1 | 8/2002 | Shanbrom |
| 2002/0119437 A1 | 8/2002 | Grroms et al. |
| 2002/0127719 A1 | 9/2002 | Stone |
| 2002/0191487 A1 | 12/2002 | Sand |
| 2003/0012687 A1 | 1/2003 | Macphee et al. |
| 2003/0022149 A1 | 1/2003 | Shanbrom |
| 2003/0027125 A1 | 2/2003 | Mills et al. |
| 2003/0035843 A1 | 2/2003 | Livesey et al. |
| 2003/0036762 A1 | 2/2003 | Kerr et al. |
| 2003/0036801 A1 | 2/2003 | Schwartz et al. |
| 2003/0039673 A1 | 2/2003 | Shanbrom |
| 2003/0064090 A1 | 4/2003 | Khouri et al. |
| 2003/0065333 A1 | 4/2003 | DeMayo |
| 2003/0068815 A1 | 4/2003 | Stone et al. |
| 2003/0074065 A1 | 4/2003 | Stone |
| 2003/0129167 A1 | 7/2003 | Shanbrom |
| 2003/0135209 A1 | 7/2003 | Seedhom et al. |
| 2003/0144743 A1 | 7/2003 | Edwards et al. |
| 2003/0161897 A1 | 8/2003 | Shanbrom |
| 2003/0167062 A1 * | 9/2003 | Gambale et al. ............ 606/138 |
| 2003/0171810 A1 | 9/2003 | Steiner |
| 2003/0180181 A1 | 9/2003 | Greib et al. |

(56) References Cited

U.S. PATENT DOCUMENTS

| | | |
|---|---|---|
| 2003/0198699 A1 | 10/2003 | Shanbrom |
| 2003/0216669 A1 | 11/2003 | Lang et al. |
| 2003/0220700 A1 | 11/2003 | Hammer et al. |
| 2003/0225459 A1 | 12/2003 | Hammer et al. |
| 2003/0228692 A1 | 12/2003 | Goldstein et al. |
| 2003/0229400 A1 | 12/2003 | Masuda et al. |
| 2004/0034359 A1 | 2/2004 | Schmeiding et al. |
| 2004/0037735 A1 | 2/2004 | Depaula et al. |
| 2004/0039400 A1 | 2/2004 | Schmieding et al. |
| 2004/0048796 A1 | 3/2004 | Hariri et al. |
| 2004/0052830 A1 | 3/2004 | Konertz et al. |
| 2004/0059425 A1 | 3/2004 | Schmieding |
| 2004/0059430 A1 | 3/2004 | Kim et al. |
| 2004/0067582 A1 | 4/2004 | Lloyd et al. |
| 2004/0073223 A1 | 4/2004 | Burkinshaw |
| 2004/0076657 A1 | 4/2004 | Wolfinbarger, Jr. et al. |
| 2004/0081954 A1 | 4/2004 | Stone et al. |
| 2004/0098135 A1 | 5/2004 | Stone et al. |
| 2004/0147932 A1 | 7/2004 | Burkinshaw et al. |
| 2004/0157206 A1 | 8/2004 | Fisher et al. |
| 2004/0176771 A1 | 9/2004 | Schmieding |
| 2004/0192605 A1 | 9/2004 | Zhang et al. |
| 2004/0193154 A1 | 9/2004 | Leatherbury et al. |
| 2004/0197373 A1 | 10/2004 | Gertzman et al. |
| 2004/0204715 A1 | 10/2004 | Evans et al. |
| 2004/0230194 A1 | 11/2004 | Urbanski et al. |
| 2004/0230303 A1 | 11/2004 | Gomes et al. |
| 2004/0234507 A1 | 11/2004 | Stoen |
| 2004/0236340 A1 | 11/2004 | Cirotteau et al. |
| 2004/0243250 A1 | 12/2004 | Stone et al. |
| 2005/0013870 A1 | 1/2005 | Freyman et al. |
| 2005/0013872 A1 | 1/2005 | Freyman |
| 2005/0021044 A1 | 1/2005 | Stone et al. |
| 2005/0038520 A1 | 2/2005 | Bienette et al. |
| 2005/0043813 A1 | 2/2005 | Kusanagi |
| 2005/0043814 A1 | 2/2005 | Kusanagi et al. |
| 2005/0043819 A1 | 2/2005 | Schmidt et al. |
| 2005/0064042 A1 | 3/2005 | Vunjak-novakovic et al. |
| 2005/0064591 A1 | 3/2005 | Stone |
| 2005/0080435 A1 | 4/2005 | Smith et al. |
| 2005/0089544 A1 | 4/2005 | Khouri et al. |
| 2005/0113736 A1 | 5/2005 | Orr et al. |
| 2005/0124997 A1 | 6/2005 | Pajunk et al. |
| 2005/0137600 A1 | 6/2005 | Jacobs et al. |
| 2005/0196393 A1 | 9/2005 | Shanbrom |
| 2005/0209705 A1 | 9/2005 | Niederauer et al. |
| 2005/0222687 A1 | 10/2005 | Vunjak-novakovic et al. |
| 2005/0251268 A1 | 11/2005 | Truncale |
| 2005/0256588 A1 | 11/2005 | Sawa et al. |
| 2006/0019234 A1 | 1/2006 | Shanbrom |
| 2006/0024380 A1 | 2/2006 | Abraham et al. |
| 2006/0060209 A1 | 3/2006 | Shepard |
| 2006/0083729 A1 | 4/2006 | Kusanagi et al. |
| 2006/0127495 A1 | 6/2006 | Cheung |
| 2006/0127876 A1 | 6/2006 | Cheung |
| 2006/0131906 A1 | 6/2006 | Maurer et al. |
| 2006/0142684 A1 | 6/2006 | Shanbrom |
| 2006/0178748 A1 | 8/2006 | Dinger, III et al. |
| 2006/0193885 A1 | 8/2006 | Leonard Neethling et al. |
| 2006/0195188 A1 | 8/2006 | O'Driscoll et al. |
| 2006/0247790 A1 | 11/2006 | McKay |
| 2006/0275377 A1 | 12/2006 | Gomes et al. |
| 2007/0010897 A1 | 1/2007 | Stone |
| 2007/0043376 A1 | 2/2007 | Leatherbury et al. |
| 2007/0093896 A1 | 4/2007 | Malinin |
| 2007/0135917 A1 | 6/2007 | Malinin |
| 2007/0135918 A1 | 6/2007 | Malinin |
| 2007/0135928 A1 | 6/2007 | Malinin |
| 2007/0149982 A1 | 6/2007 | Lyons |
| 2007/0270711 A1 | 11/2007 | Gil et al. |
| 2007/0276506 A1 | 11/2007 | Troxel |
| 2007/0299517 A1 | 12/2007 | Davisson |
| 2008/0019115 A1 | 1/2008 | Park, II et al. |
| 2008/0027447 A1 | 1/2008 | Gil et al. |
| 2008/0051812 A1 | 2/2008 | Schmitz et al. |
| 2008/0058953 A1 | 3/2008 | Scarborough |
| 2008/0167653 A1 | 7/2008 | Watlington et al. |
| 2008/0195115 A1 | 8/2008 | Oren et al. |
| 2008/0200915 A1 | 8/2008 | Globerman et al. |
| 2008/0243028 A1 | 10/2008 | Howard et al. |
| 2008/0243029 A1 | 10/2008 | Howard et al. |
| 2008/0255427 A1 | 10/2008 | Satake et al. |
| 2008/0262616 A1 | 10/2008 | McKay |
| 2008/0269566 A1 | 10/2008 | Measamer et al. |
| 2008/0281081 A1 | 11/2008 | Shanbrom |
| 2008/0306608 A1 | 12/2008 | Nycz et al. |
| 2009/0024224 A1 | 1/2009 | Chen et al. |
| 2009/0047085 A1 | 2/2009 | Liao et al. |
| 2009/0054906 A1 | 2/2009 | Walthall et al. |
| 2009/0076556 A1* | 3/2009 | McGarity et al. ............ 606/281 |
| 2009/0171359 A1 | 7/2009 | Sterrett |
| 2009/0209962 A1 | 8/2009 | Jamali |
| 2009/0228031 A1 | 9/2009 | Ritter |
| 2009/0275950 A1 | 11/2009 | Sterrett et al. |
| 2009/0281550 A1 | 11/2009 | Keller |
| 2009/0299371 A1 | 12/2009 | Steiner et al. |
| 2009/0299372 A1 | 12/2009 | Steiner et al. |
| 2009/0319051 A9 | 12/2009 | Nycz et al. |
| 2010/0123325 A1* | 5/2010 | Maffeis .......................... 294/88 |
| 2010/0168750 A1 | 7/2010 | Sherman |
| 2010/0249786 A1 | 9/2010 | Schmieding et al. |
| 2010/0292704 A1 | 11/2010 | Stoffel et al. |
| 2011/0009872 A1 | 1/2011 | Mistry et al. |
| 2011/0046628 A1 | 2/2011 | Jamali |
| 2011/0054408 A1 | 3/2011 | Wei et al. |
| 2011/0137315 A1 | 6/2011 | Gil et al. |
| 2011/0144648 A1 | 6/2011 | Gil et al. |
| 2011/0208193 A1 | 8/2011 | Gil et al. |
| 2012/0053588 A1 | 3/2012 | Lozier et al. |
| 2012/0053642 A1 | 3/2012 | Lozier et al. |

FOREIGN PATENT DOCUMENTS

| | | |
|---|---|---|
| AU | 717552 | 3/1998 |
| DE | 2411618 A1 | 4/1975 |
| DE | 2830566 A1 | 1/1980 |
| DE | 2933174 A1 | 4/1980 |
| DE | 4317448 A1 | 11/1994 |
| DE | 19503504 A1 | 3/1996 |
| EP | 0307241 A2 | 3/1989 |
| EP | 0493698 A1 | 7/1992 |
| EP | 0508710 A1 | 10/1992 |
| EP | 0399647 B1 | 12/1995 |
| EP | 0768332 A1 | 4/1997 |
| EP | 0779320 A2 | 6/1997 |
| EP | 0815809 A2 | 1/1998 |
| EP | 0824893 A2 | 2/1998 |
| EP | 0824893 B1 | 2/1998 |
| EP | 0871414 A1 | 10/1998 |
| EP | 0584195 B1 | 9/2001 |
| EP | 1006957 B1 | 5/2003 |
| EP | 0740555 B1 | 3/2004 |
| EP | 0814710 B1 | 4/2004 |
| EP | 1237511 B1 | 9/2004 |
| EP | 1452150 A1 | 9/2004 |
| EP | 1637037 A2 | 3/2006 |
| EP | 1234552 B1 | 8/2006 |
| EP | 1698358 A1 | 9/2006 |
| FR | 2700462 A1 | 7/1994 |
| FR | 2860423 A1 | 4/2005 |
| GB | 1565340 A | 4/1980 |
| GB | 2175506 A | 12/1986 |
| JP | 3178652 A | 2/1991 |
| JP | 4303450 A | 10/1992 |
| JP | 9122226 A | 5/1997 |
| JP | 10251492 A | 9/1998 |
| JP | 10513386 A | 12/1998 |
| RU | 2088240 C1 | 8/1997 |
| WO | WO-9106213 A1 | 5/1991 |
| WO | WO-9211046 A1 | 7/1992 |
| WO | WO-9212631 A1 | 8/1992 |
| WO | WO-9315694 A1 | 8/1993 |
| WO | WO-9426211 A1 | 11/1994 |
| WO | WO-9502350 A1 | 1/1995 |

(56) References Cited

FOREIGN PATENT DOCUMENTS

| WO | WO-9612509 A1 | 5/1996 |
|----|---------------|--------|
| WO | WO-9624302 A1 | 8/1996 |
| WO | WO-9624310 A1 | 8/1996 |
| WO | WO-9627333 A1 | 9/1996 |
| WO | WO-9634955 A1 | 11/1996 |
| WO | WO-9725942 A1 | 7/1997 |
| WO | WO-9746665 A1 | 12/1997 |
| WO | WO-9802578 A1 | 1/1998 |
| WO | WO-9834569 A1 | 8/1998 |
| WO | WO-9834596 A2 | 8/1998 |
| WO | WO-9840027 A1 | 9/1998 |
| WO | WO-9846165 A1 | 10/1998 |
| WO | WO-9856317 A1 | 12/1998 |
| WO | WO-9921497 A1 | 5/1999 |
| WO | WO-9947080 A1 | 9/1999 |
| WO | WO-9944533 A1 | 10/1999 |
| WO | WO-9951170 A1 | 10/1999 |
| WO | WO-0029037 A1 | 5/2000 |
| WO | WO-0041739 A1 | 7/2000 |
| WO | WO-0047131 A1 | 8/2000 |
| WO | WO-0047132 A1 | 8/2000 |
| WO | WO-0105336 A1 | 1/2001 |
| WO | WO-0108715 A1 | 2/2001 |
| WO | WO-0130276 A1 | 5/2001 |
| WO | WO-0143667 A1 | 6/2001 |
| WO | WO-0154619 A1 | 8/2001 |
| WO | WO-0182993 A2 | 11/2001 |
| WO | WO-0191671 A1 | 12/2001 |
| WO | WO-0224244 A2 | 3/2002 |
| WO | WO-02089711 A1 | 11/2002 |
| WO | WO-03023272 A1 | 3/2003 |
| WO | WO-03097809 A2 | 11/2003 |
| WO | WO-2004017731 A1 | 3/2004 |
| WO | WO-2004047622 A2 | 6/2004 |
| WO | WO-2004052098 A1 | 6/2004 |
| WO | WO-2004075727 A2 | 9/2004 |
| WO | WO-2004075940 A1 | 9/2004 |
| WO | WO-2004100841 A1 | 11/2004 |
| WO | WO-2004103224 A1 | 12/2004 |
| WO | WO-2005023321 A2 | 3/2005 |
| WO | WO-2005038016 A1 | 4/2005 |
| WO | WO-2005063314 A1 | 7/2005 |
| WO | WO-2005092208 A1 | 10/2005 |
| WO | WO-2005094694 A2 | 10/2005 |
| WO | WO-2005112627 A1 | 12/2005 |
| WO | WO-2005118014 A2 | 12/2005 |
| WO | WO-2006026325 A2 | 3/2006 |
| WO | WO-2006026325 A3 | 3/2006 |
| WO | WO-2006026981 A1 | 3/2006 |
| WO | WO-2006074373 A2 | 7/2006 |
| WO | WO-2006092718 A2 | 9/2006 |
| WO | WO-2008147692 A1 | 12/2008 |
| WO | WO-2009114524 A1 | 9/2009 |
| WO | WO-2010092100 A1 | 8/2010 |
| WO | WO-2011008968 A1 | 1/2011 |

OTHER PUBLICATIONS

"U.S. Appl. No. 10/149,853, Notice of Allowance mailed Oct. 5, 2004", 7 pgs.
"U.S. Appl. No. 10/149,853, Preliminary Amendment mailed Oct. 17, 2002", 6 pgs.
"U.S. Appl. No. 10/149,853, Response filed Jul. 6, 2004 to Non Final Office Action mailed Apr. 13, 2004", 9 pgs.
"U.S. Appl. No. 11/705,575, Non Final Office Action mailed Mar. 16, 2005", 8 pgs.
"U.S. Appl. No. 11/705,575, Non Final Office Action mailed Sep. 15, 2011", 7 pgs.
"U.S. Appl. No. 11/705,575, Notice of Allowance mailed May 15, 2012", 5 pgs.
"U.S. Appl. No. 11/705,575, Notice of Non-Compliant Amendment mailed Jan. 7, 2011", 3 pgs.
"U.S. Appl. No. 11/705,575, Notice of Non-Compliant Amendment mailed Oct. 29, 2010", 3 pgs.

"U.S. Appl. No. 11/705,575, Preliminary Amendment filed Feb. 12, 2007", 14 pgs.
"U.S. Appl. No. 11/705,575, Response filed Feb. 7, 2011 to Notice of Non-Compliant Amendment mailed Jan. 7, 2011", 22 pgs.
"U.S. Appl. No. 11/705,575, Response filed Sep. 15, 2010 to Non Final Office Action mailed Mar. 16, 2010", 13 pgs.
"U.S. Appl. No. 11/705,575, Response filed Nov. 29, 2010 to Notice of Non-Compliant Amendment mailed Oct. 29, 2010", 14 pgs.
"U.S. Appl. No. 11/705,575, Response filed Dec. 15, 2011 to Non Final Office Action mailed Sep. 15, 2011", 14 pgs.
"U.S. Appl. No. 11/705,575, Revised Preliminary Amendment filed Sep. 15, 2010 in Response to Office Action mailed Mar. 16, 2010", 11 pgs.
"U.S. Appl. No. 11/753,102, Advisory Action filed Dec. 10, 2010", 3 pgs.
"U.S. Appl. No. 11/753,102, Final Office Action mailed Aug. 3, 2010", 14 pgs.
"U.S. Appl. No. 11/753,102, Non Final Office Action mailed Jan. 4, 2010", 13 pgs.
"U.S. Appl. No. 11/753,102, Response filed May 4, 2010 to Non Final Office Action mailed Jan. 4, 2010", 13 pgs.
"U.S. Appl. No. 11/753,102, Response filed Nov. 23, 2009 to Restriction Requirement mailed Oct. 30, 2009", 12 pgs.
"U.S. Appl. No. 11/753,102, Response filed Dec. 3, 2010 to Final Office Action mailed Aug. 3, 2010", 15 pgs.
"U.S. Appl. No. 11/753,102, Restriction Requirement mailed Oct. 30, 2009", 9 pgs.
"U.S. Appl. No. 11/759,679, Final Office Action mailed Oct. 7, 2010", 17 pgs.
"U.S. Appl. No. 11/759,679, Non Final Office Action mailed Feb. 26, 2010", 14 pgs.
"U.S. Appl. No. 11/759,679, Response filed Jun. 28, 2009 to Non Final Office Action mailed Feb. 26, 2010", 13 pgs.
"U.S. Appl. No. 11/759,679, Response filed Oct. 30, 2009 to Restriction Requirement mailed Sep. 4, 2009", 3 pgs.
"U.S. Appl. No. 11/759,679, Restriction Requirement mailed Sep. 4, 2009", 6 pgs.
"U.S. Appl. No. 12/045,416, Final Office Action mailed Feb. 27, 2012", 13 pgs.
"U.S. Appl. No. 12/045,416, Non Final Office Action mailed Aug. 4, 2011", 12 pgs.
"U.S. Appl. No. 12/045,416, Response filed Jun. 2, 2011 to Restriction Requirement mailed May 11, 2011", 13 pgs.
"U.S. Appl. No. 12/045,416, Response filed Jul. 17, 2012 to Final Office Action mailed Feb. 17, 2012", 19 pgs.
"U.S. Appl. No. 12/045,416, Response filed Dec. 5, 2011 to Non Final Office Action mailed Aug. 4, 2011", 18 pgs.
"U.S. Appl. No. 12/045,416, Restriction Requirement mailed May 11, 2011", 8 pgs.
"U.S. Appl. No. 12/196,831, Advisory Action mailed Jan. 21, 2011", 3 pgs.
"U.S. Appl. No. 12/196,831, Advisory Action mailed Jul. 5, 2012", 3 pgs.
"U.S. Appl. No. 12/196,831, Examiner Interview Summary mailed Feb. 6, 2012", 18 pgs.
"U.S. Appl. No. 12/196,831, Final Office Action mailed Apr. 12, 2012", 17 pgs.
"U.S. Appl. No. 12/196,831, Final Office Action mailed Nov. 12, 2010", 9 pgs.
"U.S. Appl. No. 12/196,831, Non Final Office Action mailed Jul. 9, 2010", 7 pgs.
"U.S. Appl. No. 12/196,831, Non Final Office Action mailed Oct. 6, 2011", 8 pgs.
"U.S. Appl. No. 12/196,831, Response filed Jan. 10, 2011 to Final Office Action mailed Nov. 12, 2010", 10 pgs.
"U.S. Appl. No. 12/196,831, Response filed Feb. 1, 2012 to Non Final Office Action mailed Oct. 6, 2011", 15 pgs.
"U.S. Appl. No. 12/196,831, Response filed Jun. 12, 2012 to Final Office Action mailed Apr. 12, 2012", 14 pgs.
"U.S. Appl. No. 12/196,831, Response filed Jun. 21, 2010 to Restriction Requirement mailed Jun. 8, 2010", 8 pgs.
"U.S. Appl. No. 12/196,831, Response filed Sep. 12, 2012 to Advisory Action mailed Jul. 5, 2012", 16 pgs.

(56) References Cited

OTHER PUBLICATIONS

"U.S. Appl. No. 12/196,831, Response filed Oct. 7, 2010 to Non Final Office Action mailed Jul. 9, 2010", 11 pgs.
"U.S. Appl. No. 12/196,831, Restriction Requirement mailed Jun. 8, 2010", 7 pgs.
"U.S. Appl. No. 12/873,030, Non Final Office Action mailed Oct. 30, 2012", 17 pgs.
"U.S. Appl. No. 12/873,030, Response filed Feb. 28, 2013 to Non Final Office Action mailed Oct. 30, 2012", 14 pgs.
"U.S. Appl. No. 12/873,030, Response filed Jul. 27, 2012 to Restriction Requirement mailed Jul. 10, 2012", 7 pgs.
"U.S. Appl. No. 12/873,030, Restriction Requirement mailed Jul. 10, 2012", 6 pgs.
"U.S. Appl. No. 12/873,049, Notice of Allowance mailed Mar. 25, 2013", 9 pgs.
"U.S. Appl. No. 12/873,049, Notice of Allowance mailed Nov. 14, 2012", 13 pgs.
"U.S. Appl. No. 12/873,049, Response filed Jul. 27, 2012 to Restriction Requirement mailed Jul. 10, 2012", 8 pgs.
"U.S. Appl. No. 12/873,049, Restriction Requirement mailed Jul. 10, 2012", 5 pgs.
"Aseptically-Processed Bone and Connective Tissue", American Red Cross, (1995), 2 pgs.
"Australian Application Serial No. 200116857, Office Action mailed Feb. 13, 2004", 2 pgs.
"Canadian Application Serial No. 00979315.9, Office Action mailed Jan. 24, 2007", 3 pgs.
"Canadian Application Serial No. 00979315.9, Response filed Jul. 23, 2007 to Office Action mailed Jan. 24, 2007", 14 pgs.
"Disinfectant Details and Their Uses", The Master Budgerigar Breeder <http://www.bestofbreeds.net/masterbreeder/chap6/chap6disinfectant6.htm>, (1991), 1-14.
"European Application Serial No. 04020622.9, European Search Report mailed Nov. 29, 2004", 6 pgs.
"European Application Serial No. 04020622.9, Office Action mailed Oct. 20, 2005", 3 pgs.
"European Application Serial No. 04020622.9, Response filed Apr. 13, 2006 to Office Action mailed Oct. 20, 2005", 12 pgs.
"High Pressure Process", (1991), 1-14.
"International Application Serial No. PCT/CH2000/000659, International Preliminary Examination Report mailed Mar. 20, 2002", 15 pgs.
"International Application Serial No. PCT/CH2000/000659, International Search Report mailed Jan. 2, 2001", 8 pgs.
"International Application Serial No. PCT/US2008/063582, International Preliminary Report on Patentability mailed Nov. 24, 2009", 8 pgs.
"International Application Serial No. PCT/US2008/063582, International Search Report mailed Oct. 9, 2008", 3 pgs.
"International Application Serial No. PCT/US2008/063582, Written Opinion mailed Oct. 9, 2008", 7 pgs.
"International Application Serial No. PCT/US2008/064653, International Search Report mailed Sep. 7, 2009", 3 pgs.
"International Application Serial No. PCT/US2008/064653, Written Opinion mailed Sep. 7, 2009", 8 pgs.
"International Application Serial No. PCT/US2009/036661, International Preliminary Report on Patentability mailed Sep. 14, 2010", 9 pgs.
"International Application Serial No. PCT/US2009/036661, International Search Report mailed Jun. 12, 2009", 4 pgs.
"International Application Serial No. PCT/US2009/036661, Written Opinion mailed Jun. 12, 2009", 8 pgs.
"Japanese Application Serial No. 2000-544609, Office Action mailed Jan. 5, 2010", 9 pgs.
"Japanese Application Serial No. 2000-544609, Office Action mailed Mar. 24, 2009", 8 pgs.
"Japanese Application Serial No. 2000-544609, Office Action mailed Aug. 5, 2008", 5 pgs.
"Japanese Application Serial No. 2000-544609, Office Action mailed Nov. 2, 2010", 7 pgs.
"Japanese Application Serial No. 2000-544609, Response filed Apr. 27, 2010 to Office Action mailed Jan. 24, 2010", 8 pgs.
"Japanese Application Serial No. 2000-544609, Response filed Jun. 11, 2009 to Office Action mailed Mar. 24, 2009", 14 pgs.
"Japanese Application Serial No. 2000-544609, Response filed Oct. 28, 2008 to Office Action mailed Aug. 5, 2008", 14 pgs.
"Macro Sensors", LVDT Basics, Technical Bulletin 0103, (Jan. 31, 2003), 4.
"Omnicide 14 Day Glutaraldehyde Disinfectant Gallon", (Accessed Mar. 6, 2008), 1-2.
"Omnicide—The DEFRA approved disinfectant to kill Avian Influenza", The Coventry Group, (2007), 1-2.
"Resorbable, Cylindrical Scaffold to Support Healing of Tissue", TruFit BGS Plugs, Bone Graft Substitute Plugs, Publication # 6100048, OsteoBiologics, Inc. San Antonio, TX USA, (2004), 2 pgs.
"Single Use OATS (Osteochondral Autograft Transfer System) Surgical Technique", Arthrex, Inc., Naples, FL, USA, (2005), 6 pgs.
"Standards for Tissue Banking", American Association of Tissue Banks, 12th Edition, (2008), 21 pgs.
"Trough", Merriam-Websters Dictionary Definition, http://www.merriam-webster.com/dictionary/trough, (Nov. 2010), 3 pgs.
Aichroth, et al., "Biologicl and Mechanical Problems of Osteoarticular Allografting: The Relation to Clinical Organ Transplantation", The Journal of the Western Pacific Orthopaedic Association, vol. VIII, No. 2, London England, No Image Available, (1971), 25-70.
Akens, "In-viro and in-vivo studies of osteochondral transplants pretreated with photo-oxidation", Ph.D. Thesis, (2002), 1-100.
Akens, Margarete K, et al., "Long term in-vivo studies of a photo-oxidized bovine osteochondral transplant in sheep.", BMC Musculoskeletal Disorders, vol. 2, No. 9, (2001), 12 pgs.
Albee, Fred H, "Bone Surgery With Machine Tools", Scientific American vol. 154.4, (Apr. 1936), 178-181.
Bakay, et al., "A mushroom-shaped osteochondral patella allograft", International Orthopaedics (SICOT) 20, (1996), 370-372.
Bakay, et al., "Osteochondral resurfacing of the knee joint with allograft", International Orthopaedics (SICOT) 22, (1998), 277-281.
Bakay, et al., "The alternatives of the application of human lyophillized spongiosa and bone-matrix gelatin", Orvosi Hetilap, vol. 136, No. 35, Budpest, (1995), 1891-1896.
Baragi, et al., "Transplantation of adenvirally transduced allogeneic chondrocytes into articular cartilage defects in vivo", Osteoarthritis and cartilage, vol. 5, (1997), 275-282.
Barber, et al., "COR Osteochondral Repair System", Osteobiologics, Inc., (2006), 17 pgs.
Barber, et al., "Osteochondral Repair System", www.obi.com, (2006), 1-17.
Barber, F. Alan, "An Arthroscopic Technique for Repair of Osteochondral Defects", The New Generation in Osteochondral Transplantation, DePuy Mitek, Inc., Raynham, MA USA, (2007), 9 pgs.
Barber, F. Alan, et al., "Osteochondral Repair System", <www.obi.eomlproducts_TruFit.htm>, 17 pgs, Sep. 11, 2006.
Bar-Shavit, Z., et al., "Glucocorticoids Modulate Macrophage Surface Oligo saccharides and Their Bone Binding Activity", J. Clin. Invest., vol. 73, (1984), 1277-1283.
Beaver, R. J, et al., "Fresh Osteochondral Allografts for Post-Traumatic Defects in the Knee", The Journal of Bone and Joint Surgery, vol. 74-8, No. 1, (1992), 105-110.
Bobic, V, "Arthroscopic osteochondral autograft transplantation in anterior cruciate ligament reconstruction: a preliminary clinical study", Knee Surg, Sport Traumatol, Arthroscopy 3, (1996), 262-264.
Bodo, G., et al., "Arthroscopic Autologous Osteochondral Mosaicplasty for the Treatment of Subchondral Cystic Lesion in the Medial Femoral Condyle in a Horse", Acta Veternaria Hungarica, vol. 48(3), (2000), 343-354.
Bos, et al., "Immune Responses of Rats to Frozen Bone Allografts", The Journal of Bone and Joint Surgery 65A(2), (1983), 239-246.
Brighton, et al., "Articular Cartilage Preservation and Storage", Arthritis and Rheumatism 22(10), (1979), 1093-1101.

(56) References Cited

OTHER PUBLICATIONS

Brooks, et al., "Immunological Factors in Homogenous Bone Transplantation", The Journal of None and Joint Surgery 45(8), (1963), 1617-1626.

Bugbee, "Fresh Osteochondral Allografts", The Journal of Knee Surgery 15(3), (2002), 191-195.

Bugbee, et al., "Osteochondral Allograft Transplantation", Complex Topics in Knee Surgery, vol. 18, No. 1, (1999), 67-75.

Bugbee, William D, "Fresh Osteochondral Allografts", Seminars in Arthroplasty, vol. 11, No. 4, No Image Available, (2000), 221-226.

Burba, et al., "An arthroscopic biopsy procedure for obtaining osteochondral samples from the equine midcarpal joint", Journal of Investigative Surgery, vol. 5, (1992), 343-359.

Calandruccio, et al., "Proliferation, Regeneration, and Repair of Articular Cartilage of Immature Animals", J. Bone Joint Surg, vol. 44-A, No. 3, (1962), 431-455.

Chalmers, J, "Transplantation immunity in bone homografting", The Journal of Bone and Joint Surgery, vol. 41B, No. 1, No Image Available, (1959), 160-179.

Chu, et al., "Articular Cartilage Transplantation—Clinical Results in the Knee", Clinical Orthoaedics and Related Research, (1991), 139-145.

Clarke, Ian C, "Quantitative measurement of human articular surface topography in vitro by profile recorder and stereomicroscopy techniques", Journal of Microscopy, vol. 97, Pl. 3, (Apr. 1973), 309-314.

Convery, et al., "Fresh osteochondral allografting of the femoral condyle", Clinical Orthopaedics and Related Research No. 273, (1991), 139-145.

Convery, et al., "Long-Term Survival of Chondrocytes in an Osteochondral Articular Cartilage Allograft", A Case Report 78(7), (1996), 1082-1087.

Convery, F.R., et al., "The Repair of Large Osteochondral Defects", An Experimental Study in Horses, Clin. Orthrop. 82., (1972), 253-262.

Cornell, et al., "A biosensor that uses ion-channel switches", Nature vol. 387, (Jun. 1997), 580-583.

Csonge, Lajos, et al., "Banking of Osteochodral allografts. Part I. Viability assays adapted for osteochondral and cartilage studies", Cell and Tissue Banking 3, (2002), 151-159.

Csonge, Lajos, et al., "Banking of Osteochondral Allografts, Part II. Preservation of Chondrocyte Viability During Long-Term Storage", Cell and Tissue Banking 3, (2002), 161-168.

Czitrom, et al., "Bone and Cartilage Allotransplantation: Review of 14 Years of Research and Clinical Studies", Clinical Orthopedics and Related Research, (1986), 141-145.

Delloye, et al., "Osteochondral Allografts in Arm and Forearm Surgery", Acta Orthopaedica Belgica, vol. 57, (1991), 75-83.

Desjardins, et al., "Incorporation of Fresh and Cryopreserved Bone in Osteochondral Autografts in the Horse", Veterinary Surgery, vol. 20, No. 6, (1991), 446-452.

Donald, Paul J, "Cartilage Grafting in Facial Reconstructions with Special Consideration of Irradiated Grafts", Laryngoscope, vol. 96, (1986), 786-806.

Ehalt, W, "Bisherige Erfahrungen mit dem plastischen Ersatz von Gelenkknorpel aus der Knochenbank", Verh. Dtsch. Orthop. Ges. 43, (1955), 107-109.

Ehalt, W., et al., "Gelenkknorpel-Plastik", Langenbecks Arch. Kiln. Chir. 299, (1962), 768-774.

Ehalt, Walther M, "Grafting of joint-cartilage Bone-Blocks from the bank", VI. Congr. Soc. Internat. Chir. Orthop. Traumatol. S., (1954), 419-421.

Elves, et al., "A Study of the Humoral Immune Response to Osteoarticular Allografts in the Sheep", Clin. exp. Immunol., vol. 17, (1974), 497-508.

Flynn, et al., "Osteoarticular Allografts to Treat Distal Femoral Osteonecrosis", Clin. Orthop. Rel. Res., No. 303, (1994), 38-43.

Friedlaender, et al., "Studies on the antigenicity of bone. I. Freeze-dried and deep-frozen bone allografts in rabbits", The Journal of Bone & Joint Surgery, vol. 58, (1976), 854-858.

Friedlaender, Gary E, "Immune Responses to Osteochondral Allografts", Clinical Orthopaedics and Related Research, No. 174, (1983), 58-68.

Garrett, John C, "Fresh Osteochondral Allografts for Treatment of Articular Defects in Osteochondritis Dissecans of the Lateral Femoral Condyle in Adults", Clinical Orthopaedics and Related Research, 303, (1994), 33-37.

Garrett, John C, "Osteochondral Allografts", Instructional Course Lectures, vol. 42, (1993), 355-358.

Garrett, John C, "Osteochondral Allografts for Reconstruction of Articular Defects of the Knee", AAOS Instructional Course Lectures, 27, (1998), 517-522.

Garrett, John C, "Treatment of Osteochondral Defects of the Distal Femur with Fresh Osteochondral Allografts: A Preliminary Report", Arthroscopy: The Journal of Arthroscopic and Related Surgery 2(4), (1986), 222-226.

Ghazavi, M. T, et al., "Fresh Osteochondral Allografts for Post-Traumatic Osteochondral Defects of the Knee", J. Bone Joint Surg., 79-B, (1997), 1008-1013.

Gould, Nathaniel, "Trephining Your Way", Orthopedic Clinics of North America, vol. 4, No. 1, (1973), 157-164.

Gross, "Use of Fresh Osteochondral Allografts to Replace Traumatic Joint Defects", Allografts in Orthopaedic Practice Ch 5, (1992), 67-82.

Guhl, James F, "Chapter 21: The Impact of Arthroscopy on Osteochondritis Dissecans", Operative Arthroscopy, (1991), 297-317.

Hangody, L, et al., "Autogenous osteochondral grafting in the knees of German Shepherd dogs: Radiographic and histological analysis", Hungarian Review of Sports Medicine 35, (1994), 117-123.

Hangody, L, et al., "Treatment of localized chondral and osteochondral defects in the knee by a new autogenous osteochondral grafting tenique", Hungarian Review of Sports Medicine 35, (1994), 241-246.

Hangody, Laszlo, "Arthroscopic autogeous osteochondral mosaicplasty for the treatment of femoral condylar articular defects: A preliminary report", Knee Surg, Sports Traumatol, Arthrosc 5, (1997), 262-267.

Hangody, Laszlo, et al., "Artoszkopos autolog osteochondralis mozaikplastica (Arthroscopic autogenous osteochondral mosaicplasty)", Hungarian Journal of Traumatology and Orthopaedics 39, (1996), 49-54.

Hangody, Laszlo, et al., "Autogenous Osteochondral Graft Technique for Replacing Knee Cartilage Defects in Dogs", Autogenous Osteochondral Mosaicplasty—Orthopaedics International Ed., vol. 5, No. 3, (1997), 175-181.

Hangody, Laszlo, "Autologous osteochondral mosaic-like graft technique for replacing weight bearing cartilage defects", 7th Congress of ESSTKSA, Abstract Only, (1996), 3 pgs.

Hangody, Laszlo, et al., "Autologous Osteochondral Mosaic-Plasty", Review of Osteology 3, (1996), 70-73.

Hangody, Laszlo, "Chapter 13: Autogenous Osteochondral Mosaicplasty for the Treatment of Focal Chondral and Osteochondral Defects of the Femoral Condyles", Knieinstabilitat und Knorpelschaden, (1998), 97-106.

Hangody, Laszlo, "Mosaic-plasty in Clinical Practice", Review of Osteology 4, (1996), 32-36.

Hangody, Laszlo, et al., "Mosaicplasty for the Treatment of Articular Cartilage Defects: Application in Clinical Practice", Orthopedics 21(7), (1998), 751-756.

Hangody, Laszlo, et al., "Mosaicplasty for the treatment of osteochondritis dissecans of the knee", [Online]. Retrieved from the Internet: <URL: http://www.egydoc.com/Sites/Arthroclub/AC_Files/Articles/article39.pdf>, (Accessed Nov. 8, 2005), 9 pgs.

Hangody, Laszlo, et al., "New Method in Treatment of Sever Local Cartilage Damage in the Knee Joint (Eine neue Methode in der Behandlung von schweren, lokalen Knorpelschaden im Kniegelenk", Osteosynthese International 5, (1997), 316-321.

Hangody, Laszlo, et al., "Osteochondral Grafting Using the Smith & Nephew Mosaicplasty System", Mosiacplasty Autogenous Osteochondral Grafting System, Knee Series, Technique Guide, (2001, 2005), 12 pgs.

(56) References Cited

OTHER PUBLICATIONS

Hangody, Laszlo, et al., "Osteochondral Plugs: Autogenous Osteochondral Mosaicplasty for the Treatment of Focal Chondral and Osteochondral Articular Defects", Operative Techniques in Orthopaedics 7(4), (1997), 312-322.

Hangody, Laszlo, et al., "Sülyos, körülírt térdízületi porckárosodás sebészi kezelésének új lehetosége (New alternative in the treatment of sever, localized cartilage damages in the knee joint)", Hungarian Journal of Traumatology and Orthopaedics 37, (1994), 237-242.

Hangody, Laszlo, et al., "Treatment of Osteochondritis Dissecans of the Talus: Use of Mosaicplasty Technique—A Preliminary Report", Foot and Ankle International 18(10), (1997), 628-634.

Harrison, et al., "Effect of Extraction Protocols and Epidermal Growth Factor on the Cellular Repopulation of Decellularized Anterior Cruciate Ligament Allografts", Wiley Periodicals, Inc. J. Biomed Mater Res 75A, (2005), 841-854.

Hetherington, Vincent J, et al., "Immunologic Testing for Xeno-Derived Osteocartilagenous Grafts", Ohio College of Podiatric Medicine Research Foundation, (2002), 1 pg.

Hetherington, Vincent J, et al., "Immunologic Testing of xeno-derived osteochondral grafts using peripheral blood mononuclear cells from healthy human donors", BMC Musculoskeletal Disorders vol. 6, No. 36, (2005), 11 pgs.

Hetherington, Vincent J, et al., "Qualitative Histological Evaluation of Photooxidized Bovine Ostechondral Grafts in Rabbits: A Pilot Study", The Journal of Foot & Ankle Surgery, vol. 46(4), (2007), 223-229.

Hudson, et al., "Optimized Acellular Nerve Graft is Immunologically Tolerated and Supports Regeneration", Tissue Engineering 10(11/12), (2004), 1641-1652.

Hurtig, et al., "Osteochondral Dowel Transplantation for Repair of Focal Defects in the Knee: an Outcome Study Using an Ovine Model", Vet. Surgery vol. 27, (1998), 5-16.

Hurtig, M B, "Experimental use of small osteochondral grafts for resurfacing the equine third carpal bone", Equine Orthopaedics, Supp. 6, (1988), 23-27.

Hurtig, M, et al., "Surgical and analytical techniques for articular cartilage transplantation", Veterinary Surgery, The Official Journal of the American College of Veterinary Surgeons, Inc., vol. 21, No. 5, (1992), 394.

Hurtig, M, et al., "Surgical and analytical techniques for assessment of transplanted articular cartilage: A pilot study", Cryobiology, 29(6), Twenty-ninth Annual Meeting of the Society for Cryobiology Ithaca, New York, USA, (1992), 732.

Jakob, et al., "Autologous Osteochondral Grafting in the Knee: Indication, Results and Reflections", Clinical Orthopaedics and Related Research, No. 401, (2002), 170-184.

Jakob, et al., "Isolated articular cartilage lesion: repari or regeneration", Osteoarthritis and Cartilage Journal of the OsteoArthritis Research Society International, vol. 9, Supplement A, www.idealibrary.com, (2001), S3-S5.

Jamali, et al., "Donor cell survival in a fresh osteochondral allograft at twenty-nine years", The Journal of Bone & Joint Surgery, vol. 89, (2007), 166-169.

Jimenez, et al., "Experimental Studies on the Fate of Transplanted Articular Cartilage", Osteochondral Allografts, Biology, Banking and Clinical Applications, (1983), 73-79.

Kamijou, et al., "Effects of Osteocytes on Osteoinduction in the Autogenous Rib Graft in the Rat Mandible", Bone, vol. 15, No. 6, (1994), 629-637.

Kawalec-Carroll, et al., "Immunogenicity of unprocessed and photooxidized bovine and human osetochondral grafts in collagen-sensitive mice", BMC Musculo. Dis., vol. 7, (2006), 1471-2474.

Kawamura, et al., "Human Fibrin Is a Physiologic Delivery System for Bone Morphogenetic Protein", Clinical Orthopaedics and Related Research, (Oct. 1988), 302-310.

Kelley, et al., "Chondrocyte repopulation of allograft cartilage: A preliminary investigation and strategy for developing cartilage matrice for reconstruction", Otolaryngology-Head and Neck Surgery, vol. 127, No. 4, (2002), 265-270.

Kluger, et al., "Removal of the surface layers of human cortical bone allografts restores in vitro osteoclast function reduced by processing and frozen storage", Bone 32, (2003), 291-296.

Kubler, N., et al., "Bone Morphogenetic Protein-Mediated Interaction of Periosteum and Diaphysis", Clincal Orthopedics and Related Research, vol. 258, (1990), 279-294.

Kwan, et al., "Histological and Biomechanical Assessment of Articular Cartilage from Stored Osteochondrol Shell Allografts", Journal of Orthopaedic Research, vol. 7, No. 5, (1989), 637-644.

Lehman, Richard C, "Surgical Technique for Backfill of Graft Harvest Site for Osteochondral Autograft Transfer (OATS) Procedure", Osseofit Porous Tissue Matrix, BIOMET Sports Medicine, Inc., Warsaw, IN USA, (2008), 12 pgs.

Lexer, E, "Joint transplantation", Clinical Orthopaedics and Related Research, No. 197, (1985), 4-10.

Lindholm, Sam, et al., "Reconstruction of the Articular Surface by Transfixation of an Osteochondral Fragment of the Femoral Condyle Using a Bone Transplant", Scandinavian Journal of Rheumatology Supplement 44, (1982), 5-13.

Locht, et al., "Late Osteochondral Allograft Resurfacing for Tibial Plateau Fractures", The Journal of Bone and Joint Surgery 66(3), (1984), 328-335.

Mahomed, M.N., et al., "The Long-Term Success of Fresh, Small Fragment Osteochondral Alografts Used for Intraarticular Post-Traumatic Defects in the Knee Joint", Orthopedics 15, (1992), 1191-1199.

Malinin, et al., "Banking of Massive Osteoarticular and Intercalary Bone Allografts—12 Years Experience", Clinical Orthopaedics and Related Research, No. 197, (1985), 44-57.

Malinin, et al., "Cryopreservation of articular cartilage", Clinical Orthopaedics and Related Research, No. 33, (1994), 18-32.

Mankin, et al., "Clinical experience with allograft implantation", Clinical Orthopaedics and Related Research, No. 74, (1983), 69-86.

Marco, F, et al., "Osteochondral Allografts in Femoral Condyles", International Orthopaedics 17, (1993), 105-108.

Matsusue, et al., "Arthroscopic Multiple Osteochondral Transplantation to the Chondral Defect in teh Knee Associated with Anterior Cruciate Ligament Disruption", Arthroscopy: The Journal of Arthroscopic and Related Surgery, vol. 9, No. 3, (1993), 318-321.

Maury, et al., "Twenty-five year chondrocyte viability in fresh osteochondral allograft. A Case Report", The Journal of Bone & Joint Surgery, vol. 89, (1993), 159-165.

McDermott, et al., "Fresh small-fragment osteochondral allografts", Clinical Orthopaedics and Related Research, No. 197, (1985), 96-102.

McPherson, et al., "Creep Behavior of Osteochondral Grafts in Sheep", 39th Annual Meeting, Orthopaedic Research Society, (1993), 227.

Meyers, et al., "Resurfacing of the Femoral Head with Fresh Osteochondral Allograft", Clinical Orthopaedics adn Related Research, No. 197, (1985), 111-114.

Meyers, et al., "Resurfacing of the Knee with Fresh Osteochondral Allograft", J. Bone Joint Surg., (1989), 704-713.

Muller, W, "Osteochondrosis Dissecans", Progress in Orthopaedic Surgery vol. 3, (1978), 135-142.

Oakeshott, et al., "A Clinical and Histological Analysis of Failed Fresh Osteochondral Allogafts", Clinical Orthopaedics and Related Research, No. 233, (1988), 283-294.

Outerbridge, R E, "Joint Surface transplants—a preliminary report", The Journal of Western Pacific Orthopaedic Association, vol. VIII, No. 1, (1971), 1-15.

Pap, et al., "Arthroplasty of the Knee: Experimental and Clinical Experiences", The Journal of Bone& Joint Surgery, vol. 43-A, No. 4, (1961), 523-537.

Pegg, et al., "Cryopreservation of articular cartilage. Part 1: Conventional cryopreservation methods", Cryobiology 52, (2006), 335-346.

Peretti, Giuseppe M, et al., "Bonding of cartilage matrices with cultured chondrocytes: an experimental model", Journal of Orthopaedic Research 16(1), (1998), 89-95.

Pollok, et al., "Long term insulin-secretory function of islets of Langerhans encapsulated with a layer of confluent chondrocytes for immunoisolation", Pediatric Surg Int, vol. 15, (1999), 164-167.

(56) References Cited

OTHER PUBLICATIONS

Pollok, J. M., et al., "Immunoisolation of xenogeneic islets using a living tissue engineered cartilage barrier", Transplantation Proceedings, 29(4), (1997), 2131-2133.

Rechenberg, et al., "Changes in subchondral bone in cartilage resurfacing—an experimental study in sheep using different types of osteochondral grafts", OsteoArthritis and Cartilage, vol. 11, (2003), 265-277.

Robert, et al., "Studies on the Nature of the "Microfibrillar" Component of Elastic Fibers", Eur. J. Biochem. 21, (1971), 507-516.

Rodrigo, et al., "Osteocartilaginous Allografts as Compared with Autografts in teh Treatment of Knee Joint Osteocartilaginous Defects in Dogs", Clinical Orthopaedics and Related Research, No. 134, (1978), 342-349.

Roffman, Moshe, "Autogenou grafting for an osteochondral fracture of the femorale condyle", Acta Orthop Scand., vol. 66, No. 6, (1995), 571-572.

Ronsky, J L, et al., "Precise Measurement of Cat Patellofemoral Joint Surface Geometry with Multistation Digital Photogrammetry", Journal of Biomechanical Engineering, vol. 121, (Apr. 1999), 196-205.

Scbachar, et al., "Transplantation of cryopreserved osteochondral dowel allografts of focal articular defects in Ovine model", J. Orthop. Res., 17(6), (1999), 909-919.

Schachar, et al., "The effect of Cryopreservative Agents on teh Viability of Frozen Human Articular Cartilage", Canadian Orthopaedic Research Society, (1978), 79-80.

Scharchar, et al., "Fate of massive osteochondral allografts in a feline model", Osteochondral Allografts, Biology, Banking, and Clinical Applications, (1983), 81-101.

Scharchar, et al., "Metabolic and biochemical status of articular cartilage following cryopreservation and transplantation: a rabbit model", Journal of Orthopaedic Research, vol. 10, (1992), 603-609.

Shahgaldi, B F, et al., "Repair of Cartilage Lesions Using Biological Implants—A Comparative Histological and Biomechanical Study in Goats", Journal of Bone & Joint Surgery, vol. 73-5, UK, (1991), 57-64.

Shimizu, et al., "Bone resorption by isolated osteoclasts in living versus devitalized bone", Journal of Bone and Mineral Research, vol. 5, No. 4, (1990), 411-418.

Stevenson, et al., "The Fate of Articular Cartilage after Transplantation of Fresh and Cryopreserved Rissue-Antigen-Matched and Mismatched Osteochondral Allografts in Dogs", J. Bone Joint Surg. vol. 71-A, No. 9, (1989), 1297-1307.

Stone, et al., "Meniscal regeneration with copolymeric collagen scaffolds", Amer. J. Sports Med., col. 20, No. 2, (1992), 104-111.

Stone, et al., "Porcine Cartilage Transplants in the Cynomolgus Monkey: III. Transplantation of a-Galactosidase-Treated Porcine Cartilage", Transplantation, vol. 65, No. 12, (1998), 1577-1583.

Stone, et al., "Replacement of Human Anterior Cruciate Ligaments with Pig Ligaments: A Model for Ani-Non-Gal Antibody Response in Long-Term Exenotransplantation", Transplantation, vol. 83, No. 2, (2007), 211-219.

Toolan, et al., "Development of a Novel Osteochondral Graft for Cartilage Repair", John Wiley & Sons, Inc. J.Biomed Mater Res, 41, (1998), 244-250.

Verbruggen, et al., "Repair Function in Organ Cultured Human Cartilage. Replacement of Enzymatically Removed Proteoglycans During Longterm Organ Culture", The Journal of Rheumatology 12(4), (1985), 665-674.

Volkov, et al., "Use of Allogenous Articular Bone Implants as Substitutes for Autotransplants in Adult Patients", Clinical Orthopaedics and Related Research, No. 114, (1976), 192-202.

Von Rechenberg, et al., "Changes in subchondral bone in cartilage resurfacing—an experimental study in sheep using different types of osteochondral grafts", Osteoarthr. Cart., vol. 11, (2003), 265-277.

Von Rechenberg, et al., "Mosaicplasty with photooxidized, mushroom-shaped, bovine, ostechondral xenografts in experimental sheep", Vet. Comp. Orthop. Traumatol., vol. 3, (2006), 147-156.

Von Rechenberg, et al., "The use of photooxidixed, mushroom-shaped osteochondral grafts for cartilage resurfacing—a comparison to photooxidized cylindrical grafts in an experimental study in sheep", Osteoarthr. Cart., vol. 12, (2004), 201-216.

Wada, Yuichi, "Architectural remodeling in deep frozen meniscal allografts after total meniscectomy", Arthroscopy: The Journal of Arthoscopic and Related Surgery, vol. 14, No. 3, (1998), 250-257.

Wohl, G, et al., "Assessment of Bone Mechanical Integrity in Osteochondral Grafts", Orthopaedic Research Society, (1994), p. 526.

Woods, et al., "Effectiveness of three extraction techniques in the development of a decellularized bone-anterior cruciate ligament-bone graft", Biomaterials, Elsevier Science Publishers, vol. 26, No. 35, (Dec. 1, 2005), 7339-7349.

Yamashita, F., et al., "The Transplantatoin of Autogeneic Osteochondral Fragment for Osteochondritis Dissecans of the Knee", Orthopedics 15, (1992), 1191-1199.

"U.S. Appl. No. 10/149,853, Preliminary Amendment filed Sep. 14, 2012", 7 pgs.

"U.S. Appl. No. 12/196,831, Examiner Interview Summary mailed Nov. 25, 2013", 3 pgs.

"U.S. Appl. No. 12/196,831, Non Final Office Action mailed Oct. 3, 2013", 21 pgs.

"U.S. Appl. No. 12/196,831, Response filed Nov. 27, 2013 to Non-Final Office Action dated Oct. 3, 2013", 13 pgs.

"U.S. Appl. No. 12/873,030, Advisory Action mailed Oct. 16, 2013", 3 pgs.

"U.S. Appl. No. 12/873,030, Final Office Action mailed Aug. 1, 2013", 14 pgs.

"U.S. Appl. No. 12/873,030, Non Final Office Action mailed Nov. 6, 2013", 11 pgs.

"U.S. Appl. No. 12/873,030, Response filed Oct. 1, 2013 to Final Office Action mailed Aug. 1, 2013", 15 pgs.

"U.S. Appl. No. 13/619,022, Non Final Office Action mailed May 8, 2013", 6 pgs.

U.S. Appl. No. 11/753,102, Non Final Office Action mailed Feb. 26, 2014, 9 pgs.

U.S. Appl. No. 12/196,831, Final Office Action mailed Jan. 30, 2014, 19 pgs.

U.S. Appl. No. 12/873,030, Response filed Mar. 6, 2014 to Non-Final Office Action dated Nov. 6, 2013, 15 pgs.

\* cited by examiner

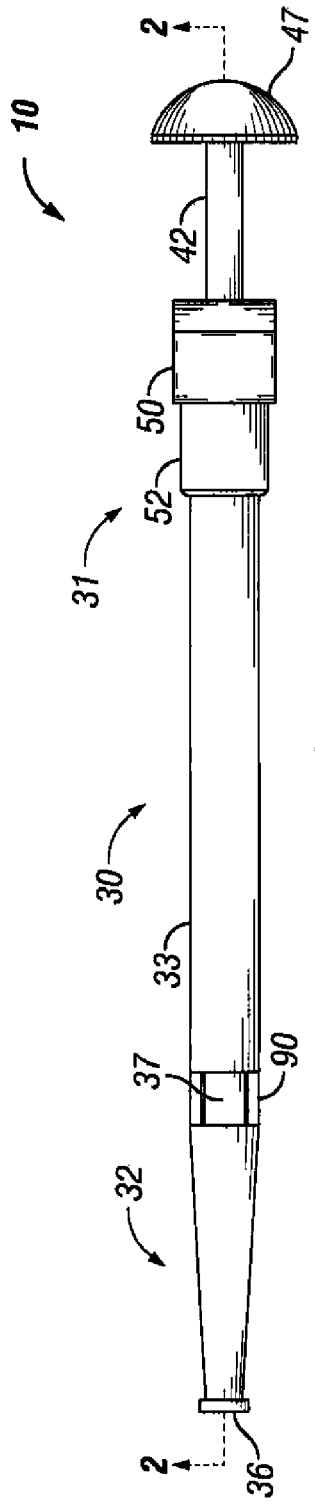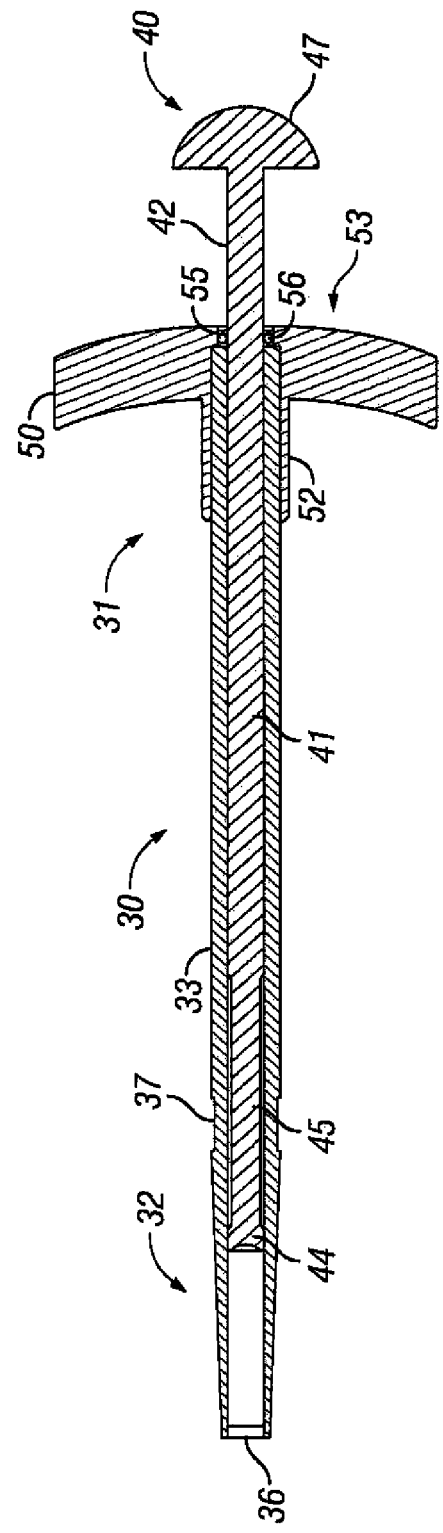

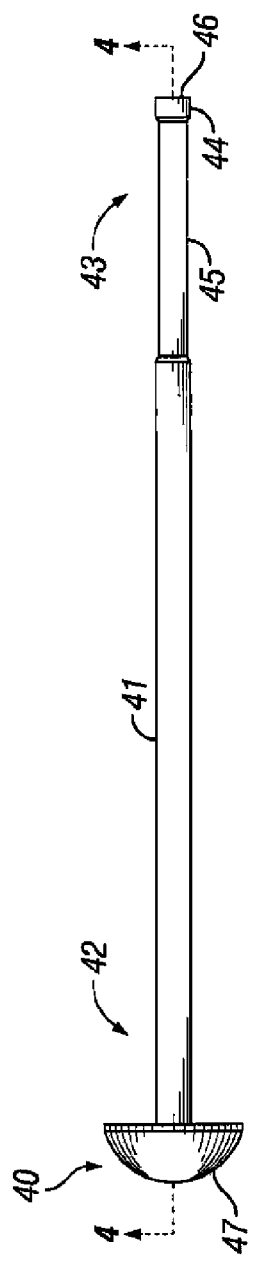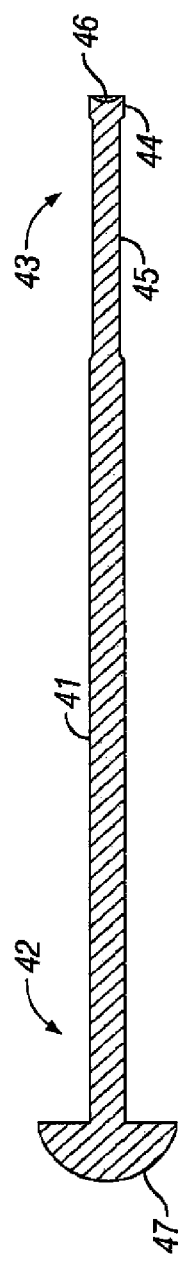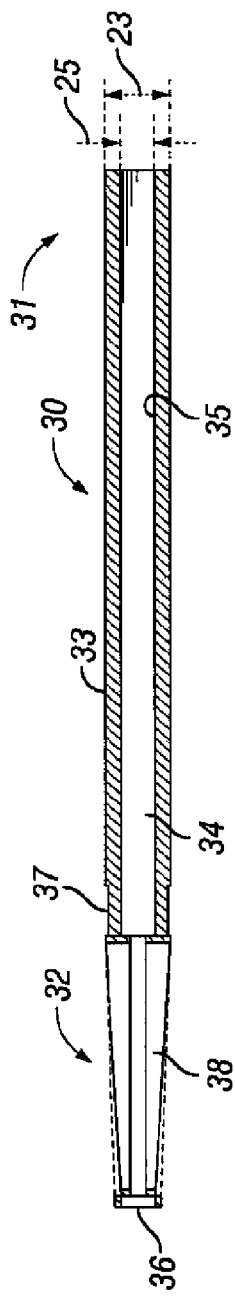
FIG. 3
FIG. 4
FIG. 5

OSTEOCHONDRAL GRAFT DELIVERY DEVICE AND USES THEREOF

This application is a continuation of and claims the benefit of priority of U.S. patent application Ser. No. 12/873,049, filed on Aug. 31, 2010, which is hereby incorporated by reference herein in its entirety.

BACKGROUND

The present invention relates to instrumentation used in implantation of an osteochondral graft, more particularly, to a delivery device used in inserting the osteochondral graft in a previously prepared hole. The invention also relates to the use of the delivery device to implant an osteochondral graft.

The delivery device of the present invention can also be used or adapted for use with bone-only or cartilage-only grafts or grafts of other construction, including artificial grafts, such as non-tissue grafts made from metals and synthetic materials. The invention has particular utility in repairing localized damage to bone and cartilage, such as lesions and other defects in an articular surface of the knee or other weight-articulating joints.

The knee and other articulating joints are susceptible to lesions and other defects. These may be the result of injuries caused by friction between opposing bone surfaces. While treatment options for these injuries lie along a continuum of care culminating in joint replacement, one treatment option is to replace the osteochondral tissue at the site of the injury with a graft of healthy tissue. Typically, autografts or allografts are employed; however, xenografts and artificial grafts, as previously described, may be employed. The surgery to implant these grafts often can be conducted arthroscopically. For this and other reasons, graft implantation may be more desirable than joint replacement.

The procedure for implanting osteochondral grafts involves creating a recipient site by removing the localized defect. Typically, this is done by forming a hole of a desired diameter (or holes, potentially, depending on the size of the defect) at the site of the damage. The hole may be bored, punched, or curetted, etc. The excised hole is then filled with a replacement osteochondral graft having a diameter corresponding to the diameter of the hole. The typical graft is cylindrical in shape and consists of a layer of cartilage over a layer of bone. Depending on the size of the damage, multiple holes of the same or different diameters may be bored and filled. Generally, in such instances, one hole will be bored and then filled before an adjacent or even overlapping hole is bored and filled.

Varied instrumentation is required throughout the surgery, both for forming the hole and implanting the replacement graft. Certain instrumentation may be tailored to the specific implant diameter.

Due to the delicate nature of the implantation procedure, in that its ultimate purpose is to repair or replace the articular surface and restore normal function to the joint, the method by which the transplanted osteochondral graft is handled and introduced into the recipient site is of particular importance. A desirable delivery device would provide a means for securely holding onto the osteochondral graft so that it is not displaced from the delivery device prematurely while simultaneously avoiding damage to the osteochondral graft.

SUMMARY

The present invention relates to instrumentation used in implantation of an osteochondral graft, more particularly, to a delivery device used in inserting the osteochondral graft in a previously prepared hole. The invention also relates to the use of the delivery device to implant an osteochondral graft.

The delivery device of the present invention can also be used or adapted for use with bone-only or cartilage-only grafts or grafts of other construction, including artificial grafts, such as non-tissue grafts made from metals and synthetic materials. The invention has particular utility in repairing localized damage to bone and cartilage, such as lesions and other defects in an articular surface of the knee or other weight-articulating joints.

According to one aspect of the invention, there is provided a delivery device for an osteochondral graft. The delivery device has a tube, a plunger and a graft retention assembly. The tube comprises a bore, having an inside diameter, that extends from a proximal end to a distal end. The inside diameter of the bore is sufficient to accept an osteochondral graft of a desired diameter. A set of apertures are located adjacent the distal end of the tube. The plunger, slidably disposed within the bore of the tube, comprises a shaft having a proximal end, distal end, and distal tip. The graft retention assembly comprises a collar and a set of tabs, which are disposed within the apertures of the tube. The tabs are biased towards each other but are capable of being displaced away from each other to receive or release the osteochondral graft. The graft retention assembly may be attached to the tube at an annular recess located along an outside diameter of the tube proximal to the apertures by means of the collar.

The delivery device may further comprise a handle positioned at the proximal end of the tube, with the handle comprising a bore extending from a proximal end to a distal end, and the bore having an inside diameter at its distal end sufficient to accept an outside diameter of the proximal end of the tube. The handle may further comprise an annular recess located at the proximal end of its bore that can accommodate a pliable material providing frictional engagement with the shaft of the plunger.

In accordance with another aspect of the present invention, there is also provided a delivery device for an osteochondral graft comprising a tube, a plunger, a graft retention assembly, and a handle. The tube comprises a bore, having an inside diameter, that extends from a proximal end to a distal end. The inside diameter of bore is sufficient to accept an osteochondral graft of a desired diameter. A set of apertures are located adjacent the distal end of the tube, and an annular recess is located along an outside diameter of the tube proximal to the apertures.

The plunger, slidably disposed within the bore of the tube, comprises a shaft having a proximal end, distal end, and distal tip. The plunger has a handle positioned at its proximal end. The plunger also has a stepped-down section of reduced relative diameter located proximal to the distal tip of the plunger shaft.

The graft retention assembly comprises a collar and a set of tabs, which are disposed within the apertures of the tube. The tabs are biased towards each other but are capable of being displaced away from each other to receive or release the osteochondral graft. The graft retention assembly is attached to the tube at the annular recess by means of the collar. Movement of the shaft of the plunger distally within the tube causes the tabs of the graft retention assembly to be displaced away from each other.

The handle, positioned at the proximal end of the tube, comprises a bore extending from a proximal end to a distal end. The bore has an inside diameter at its distal end sufficient to accept an outside diameter of the proximal end of the tube. The handle also has an annular recess located at the proximal end of its bore that can accommodate a pliable material providing frictional engagement with the shaft of the plunger.

In accordance with another aspect of the present invention, there is provided a method of implanting an osteochondral graft to a recipient site using a delivery device of the present invention. The method comprises loading the osteochondral graft into the device by inserting the distal tip of the plunger into the proximal end of the tube, moving the plunger distally in the bore of the tube until the distal tip of the plunger engages the first protrusion causing the tabs of the graft retention assembly to be displaced away from each other, and inserting the osteochondral graft into the distal end of the tube. The plunger is then moved distally in the bore of the tube further until the first protrusion no longer engages the distal tip of the plunger and the first protrusion engages the stepped-down section of the plunger, causing the tabs of the graft retention assembly to move inwardly and come in contact with and secure the osteochondral graft. To implant the osteochondral graft, the delivery device with an adjacent osteochondral graft is positioned adjacent the recipient site. The osteochondral graft is delivered by moving the plunger distally in the bore of the tube further to extrude the osteochondral graft from the delivery device.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 1 is an elevational view of a delivery device of the present invention with plunger inserted.

FIG. 2 is a cross-sectional view of the delivery device and plunger of FIG. 1.

FIG. 3 is an elevational view of a plunger of the present invention.

FIG. 4 is a cross-sectional view of the plunger of FIG. 3.

FIG. 5 is a cross-sectional view of the tube portion of a delivery device of the present invention.

Figure 6:
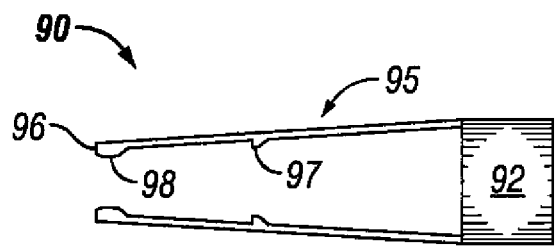
FIG. 6 is an elevational view of a spring tab assembly of the present invention.

DESCRIPTION OF PREFERRED
EMBODIMENTS

The present invention relates to instrumentation used in implantation of an osteochondral graft, more particularly, to a delivery device used in inserting the osteochondral graft in a previously prepared hole. The invention also relates to the use of the delivery device to implant an osteochondral graft. The invention has particular utility in repairing localized damage to bone and cartilage, such as lesions and other defects in an articular surface of the knee or other weight-articulating joints.

The delivery device of the present invention can be used for the implantation of grafts from various locations and sources. The delivery device of the present invention can be used or adapted for use with osteochondral grafts, bone-only grafts, or cartilage-only grafts, as well as grafts of other construction, including artificial grafts, such as non-tissue grafts made from metals and synthetic materials. Similarly, the device of the present invention can be used or adapted for use with autografts, allografts, and xenografts. The preferred use of the delivery device is for the implantation of osteochondral allografts.

The delivery device of the present invention provides a means for securely holding onto the osteochondral graft so that it is not displaced from the delivery device prematurely while simultaneously avoiding damage to the osteochondral graft.

In accordance with various embodiments of the present invention, the delivery device generally includes the following components: a tube, a plunger, a handle, and a graft retention assembly.

In the descriptions of these components that follow, various preferences for materials of construction are generally expressed. Typically, polymeric materials or stainless steel are employed. The use of other materials of construction for the components, beyond any expressed preferences, is within the scope of the present invention. Generally, any materials of construction can be used for a component as long as the function of the component is not defeated and the material of construction is considered acceptable for a surgical environment.

Similarly, in the descriptions of the components that follow, various preferences regarding whether a component is transparent, translucent, or opaque may be expressed. Notwithstanding any such expressed preferences, the optical properties of a component may be varied as long as the function of the component is not defeated and the optical properties are considered acceptable for the intended surgical environment.

It is contemplated that the delivery device of the present invention may be fabricated in various sizes to accommodate osteochondral grafts of different diameters. In some embodiments, an indicator of the delivery device to be used with an osteochondral graft of a given diameter is provided. In particularly preferred embodiments, the indicator includes a marking in the form of color-coding associated with the delivery device corresponding to a particular osteochondral graft diameter. Preferably, any other instruments within a surgical set that are tailored for use with the same osteochondral graft diameter will have similar markings.

Referring generally to FIGS. 1, 2, 5 and 11, a delivery device 10 includes tube 30. Preferably, tube 30 is formed from a polymeric material. Preferably tube 30 is transparent or translucent. Tube 30 has a proximal end 31, a distal end 32, an outside diameter 23, and a bore 34 extending from proximal end 31 to distal end 32. Bore 34 has an inside diameter 25. The inside diameter 25 of bore 34, particularly at the distal 32 end of tube 30, is of sufficient size to accept insertion of the osteochondral graft intended for use in the surgery. Desirably, the inside diameter 25 of bore 34 at the distal 32 end of tube 30 is slightly larger, preferably around 0.5 mm larger, than the diameter of osteochondral graft.

The inside diameter 25 (corresponding to inside surface 35) of bore 34 is desirably constant from proximal end 31 to distal end 32. The outside diameter 23 (corresponding to outside surface 33) of tube 30 may also be substantially constant from proximal end 31 to distal end 32. However, in various embodiments, outside surface 33 of tube 30 may have an area of reduced diameter, such as in the form of an annular recess 37 or a step. Annular recess 37 is described further in the context of apertures 38 and graft retention assembly. In various embodiments, the outer surface 33 of tube 30 may taper down toward distal end 32, for example, to achieve an area of reduced wall thickness at the distal tip 36. In certain embodiments, a 1 mm wall thickness is preferred at distal tip 36.

Located on the distal end of tube 30, proximal to distal tip 36 (between distal tip 36 and annular recess 37, when present) are apertures 38 for accommodating descending tabs of the graft retention assembly. Preferably, a set of, preferably two, apertures 38 in the form of opposing cutout panes or windows are formed in the tube 30. In alternative embodiments, a single aperture may be employed. Preferably, apertures 38 terminate distally short of distal tip 36, such that distal tip 36 exists in the form of a continuous annular surface.

Referring generally to FIGS. 2, 3 and 4, delivery device 10 has a plunger 40. Plunger 40, preferably formed from a polymeric material, is slidably disposed within bore 34 of tube 30. Plunger 40 has a shaft 41 with a proximal end 42 and distal end 43. During use of the delivery device 10, it is the distal movement of plunger 40 that causes an inserted osteochondral graft to be displaced from the delivery device 10 and implanted into the previously excised hole.

Desirably, the diameter of shaft 41 at distal tip 44 of distal end 43 substantially corresponds to the diameter of osteochondral graft. Among other benefits, this correspondence in diameter minimizes the likelihood of damage to osteochondral graft. Proximal to distal tip 44, shaft 41 has a stepped-down section 45 with a diameter smaller than that of the diameter of shaft 41 at distal tip 44. As will be described further in the context of graft retention assembly, stepped-down section 45 facilitates interaction between shaft 41 and graft retention assembly. Preferably, chamfers are provided where sections of shaft 41 having different diameters meet. In various embodiments, distal tip 44 desirably has a mating surface 46 adapted to engage osteochondral graft that is concave. In such embodiments, the concavity is preferably about 1 mm. In other embodiments, the mating surface 46 may have no curvature or may be convex.

Desirably, plunger 40 has a plunger handle 47 positioned at the proximal end 42 of shaft 41 to provide a means for gripping and depressing plunger 40. In preferred embodiments, plunger handle 47 is in the form of an enlarged button or other shape that serves as a stop against further distal movement of plunger 40. The plunger handle 47 may have an impacting surface adapted for manual depressing of the plunger 40 or for the use of a surgical hammer, mallet, or other instrument in mechanically depressing the plunger 40. The length of the plunger 40 can be tailored to achieve a desired osteochondral graft insertion depth. For example, plunger 40 can be tailored such that when it is fully depressed, the distal tip 44 may be retracted from, flush with, or extend past distal tip 36 of tube 30. For example, in certain embodiments, it may be desirable for plunger 40, when fully depressed, to remain from about 1 mm to about 2 mm retracted from distal tip 36 of tube 30. In use, this results in an implanted osteochondral graft that is about 1 mm to about 2 mm proud in the recipient hole.

Figure 9:
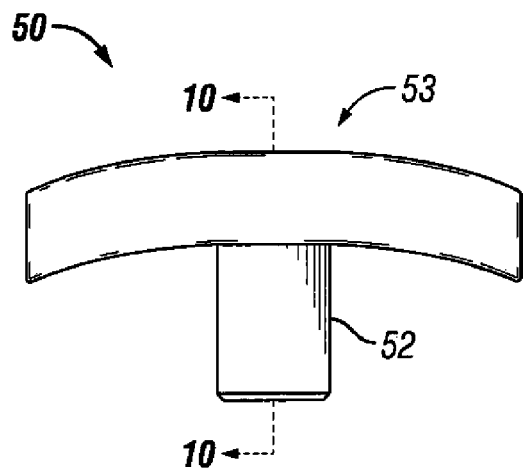
FIG. 9 is an elevational view of a handle of the present invention.
Figure 10:
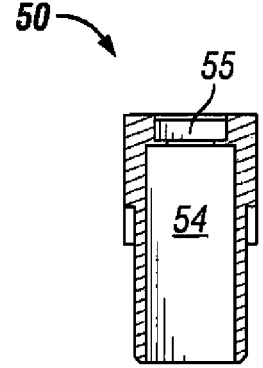
FIG. 10 is a cross-sectional view of the handle of FIG. 9.
Figure 11:
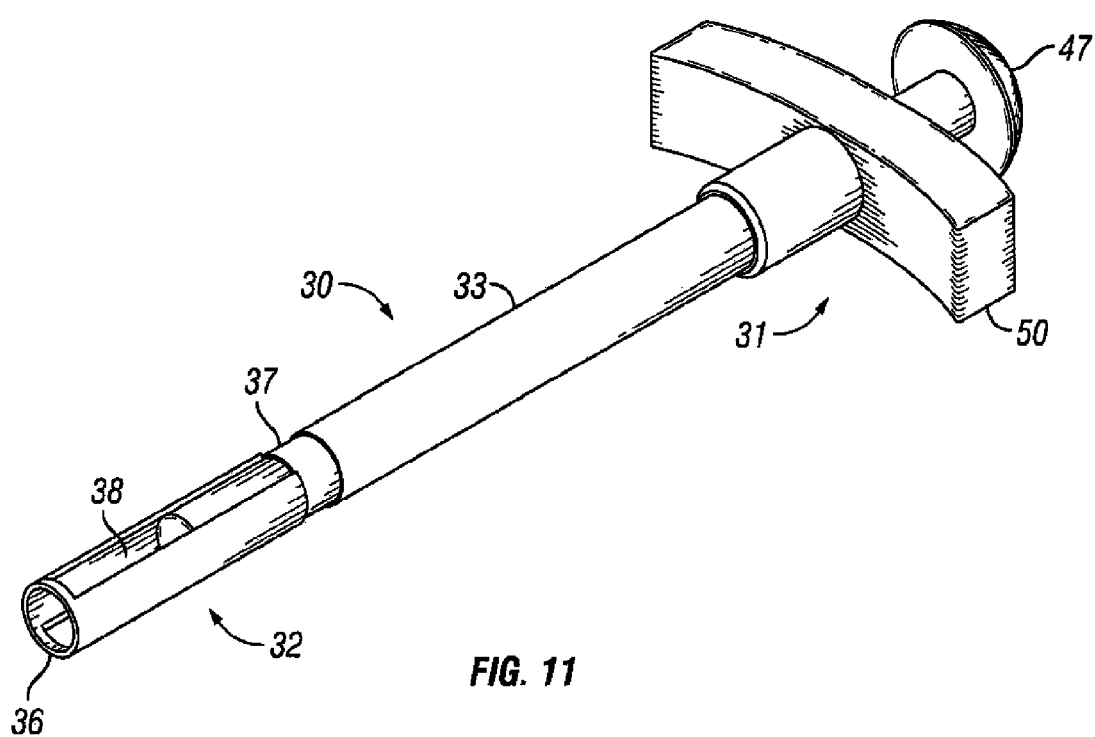
FIG. 11 is an elevational view of a delivery device of the present invention without a spring tab assembly.

Referring generally to FIGS. 1, 9 and 10, a handle 50, preferably formed from a polymeric material, is desirably positioned at the proximal end 31 of tube 30 to provide a means for gripping delivery device 10. In certain embodiments, handle 50 is integral to tube 30. Preferably, handle 50 is a separate component that is assembled onto the proximal end 31 of tube 30. In such embodiments, handle 50 can be viewed as having a distal end 52, a proximal end 53, and a bore 54 extending from the distal end 52 to the proximal end 53. In such embodiments, the distal end 52 of handle 50 is adapted for connection to the proximal end 31 of tube 30. Preferably, the proximal end 31 of tube 30 and the distal end 52 of handle 50 are sized such that the distal end 52 of handle 50 fits over the proximal end 31 of tube 30. The connection can be by friction fit, which is desirable, and/or secured by adhesive. The connection may also be by screw fit or other means. A desirable shape for handle 50 is a T-shaped contoured handle, such as depicted in FIG. 9.

Referring generally to FIG. 2, in embodiments where handle 50 is a separate component, the bore 54 at the proximal end 53 of handle 50 is of a diameter sufficient to allow slidable passage of plunger 40. Preferably, the inside diameter of bore 54 (corresponding to the inside surface of bore 54) at the proximal end 53 of handle 50 substantially corresponds to the inside diameter of tube 30. In preferred embodiments, an annular recess 55 (an area of increased inside diameter) is located within bore 54 at the proximal end 53 of handle 50. A pliable material, preferably a polymer o-ring, is disposed within the annular recess 55 that provides frictional engagement with shaft 41 of plunger 40. The o-ring acts as a seal that, during use of the delivery device 10, reduces, and preferably precludes, fluid within the joint cavity from flowing up through tube 30 and out of proximal end 31 of delivery device 10.

Figure 7:
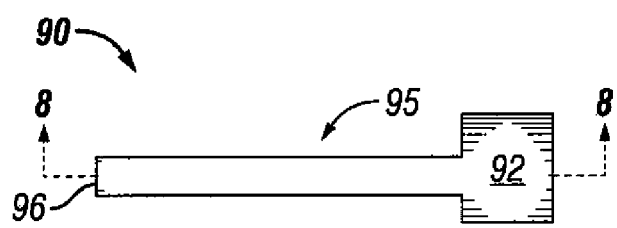
FIG. 7 is an elevational view of the spring tab assembly of FIG. 6 from a different angle.
Figure 8:
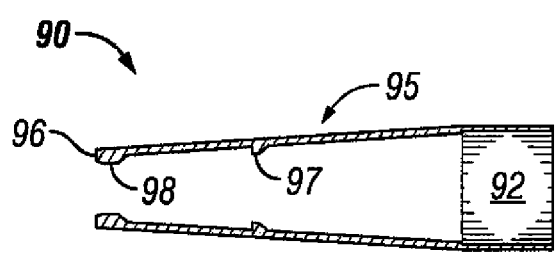
FIG. 8 is a cross-sectional view of the spring tab assembly of FIG. 7.

The delivery device 10 also has a graft retention assembly adapted for attachment to tube 30. In various embodiments, such as depicted in FIGS. 6, 7 and 8, the graft retention assembly is a spring tab assembly 90. Spring tab assembly 90 has a collar 92 that is adapted for attachment to tube 30. Spring tab assembly 90 also has a set of opposing tabs 95, corresponding preferably in number to the number of apertures 38, extending distally from collar 92, and terminating in distal tips 96. Spring tab assembly 90 is attached to tube 30 such that the tabs 95 reside within cutout panes 38. The method by which collar 92 is attached to tube 30 is not generally limited. In preferred embodiments, collar 92 is attached at and resides in annular recess 37 of tube 30. In preferred embodiments, collar 92 has a transverse slot that allows snap-fit attachment of collar 92 to tube 30.

Tabs 95 are biased, i.e., bent, towards each other when in a relaxed state but are capable of being expanded outwardly to receive and release the osteochondral graft. Desirably, the tabs 95 are bent equally from the points where they connect to the collar 92. In preferred embodiments, the extent of the bending is such that the protrusions 98 are a distance apart which is between 50-100% of the given graft diameter. Once osteochondral graft is positioned between tabs 95 and the force causing tabs 95 to expand is removed, the tabs 95 will move towards each other once again, coming in contact with and securing osteochondral graft. Preferably, the pressure exerted by the tabs 95 on the osteochondral graft is such that the tabs 95 provide enough static friction with the osteochondral graft so that it is not able to exit the delivery device 10 without the aid of the plunger 40 or other means. However, the force exerted by the tabs 95 should also not damage the osteochondral graft.

The expansion of tabs 95 to accept osteochondral graft and the subsequent inward movement of tabs 95 to secure osteochondral graft is the result of movement of shaft 41 of plunger 40 distally within tube 30. To facilitate the outward and inward movement of tabs 95, an inward facing first protrusion 97 is positioned on one or more of tabs 95. Preferably, an inward facing first protrusion 97 is positioned on each of tabs

95. First protrusion 97 is positioned proximal to distal tip 96. Preferably, first protrusion 97 is positioned half-way along the length of tabs 95.

As plunger 40 is depressed, distal tip 44 of shaft 41 first comes in contact with first protrusion 97, causing expansion of tabs 95 and facilitating insertion of osteochondral graft without risk of damage. Once the osteochondral graft has been inserted, plunger 40 is depressed further so that the first protrusion 97 engages the reduced diameter region of stepped-down section 45. First protrusion 97, depending upon the extent of the bending of tabs 95, may or may not actually come into physical contact with the shaft 41 of plunger 40 within the stepped-down section 45. At this point, tabs 95 will move towards each other once again, coming in contact with and securing osteochondral graft. In use, osteochondral graft is desirably secured within delivery device 10 with some portion of the graft extending beyond distal tip 36 of tube 30. This facilitates implantation of osteochondral graft in the previously prepared hole. For a desirable osteochondral graft having a length of about 10 mm, the graft, inserted and secured in the delivery device, extends desirably from about 0.5 mm to about 2 mm beyond distal tip 36 of tube 30, preferably about 2 mm beyond distal tip 36 of tube 30.

Due to the need for inward and outward movement of opposing fingers 95, spring tab assembly 90, and particularly opposing fingers 95, is preferably formed from stainless steel and is heat set in a bent state with opposing fingers 95 biased towards each other. In alternative embodiments, spring-biased polymeric materials or other biocompatible metals with appropriate flexibility may be employed. Other shape-memory materials may be employed.

In preferred embodiments of delivery device 10, an inward facing second protrusion 98 is positioned at or in proximity to distal tip 96 of one or more of tabs 95. Preferably, an inward facing second protrusion 98 is positioned on each of tabs 95. Second protrusion 98 facilitates gripping of osteochondral graft and reduces the likelihood of damaging osteochondral graft. A radius edge is desirably applied to the edges of the second protrusion 98 to further reduce the likelihood of damaging osteochondral graft. Desirably, a radius edge is applied to all the edges of the spring tab assembly 90. In various embodiments, a radius edge of about 1 mm is desirably employed on all edges of the spring tab assembly 90.

Having described the components of the delivery device 10, its use for implanting an osteochondral graft in a previously prepared hole is readily apparent but is described now in greater detail.

The distal tip 44 of plunger 40 is inserted into the proximal end 31 of tube 30 and moved distally within tube 30 until distal tip 44 engages first protrusion 97 of spring clip assembly 90. This causes the outward expansion of tabs 95. With tabs 95 now spread apart, a osteochondral graft is inserted, cartilage end first, into the distal end 32 of tube 30. Desirably, the osteochondral graft is left extending, preferably from about 1 mm to 2 mm, beyond distal tip 36 of tube 30.

The plunger 40 is now depressed further until first protrusion 97 is no longer in contact with the larger diameter of distal tip 44 of plunger 40. With first protrusion 97 now engaged with the reduced diameter region of stepped-down section 45, tabs 95 move towards each other, with distal tip 96, including second protrusion 98, if present, of tabs 95 coming in contact with and securing the osteochondral graft.

The delivery device 10 and the osteochondral graft are now ready to be used to implant the osteochondral graft into the recipient site, i.e., previously-prepared hole. In various embodiments of the present invention, the delivery device 10 may be used with a cannulated delivery guide that has a bore with an inside diameter sized to accommodate slidable passage of the delivery device 10. The delivery guide will preferably be made of a polymeric material but other materials of construction are contemplated. Similarly, the delivery guide may be transparent, translucent, or opaque. The delivery guide may be used to retract soft tissues (e.g., the naturally occurring fat pad) between the surgical incision or arthroscopic portal and the recipient site. In some embodiments, the delivery guide will generally be prepositioned over the prepared recipient site.

With or without the delivery guide, the delivery device 10 is positioned directly above, and preferably in contact with, the recipient site. The osteochondral graft is extruded from the delivery device 10 by depressing the plunger 40 until further distal movement of the plunger 40 is limited by the plunger handle 47, other stop, or complete insertion of the osteochondral graft in the recipient site. The delivery device 10 can then be removed from the surgical site. If the osteochondral graft remains proud, a tamp or other instrument can be used to further insert the osteochondral graft such that it is flush with the surrounding articular cartilage.

The delivery device 10 may be provided to a surgeon pre-assembled in its entirety. Alternatively, the component parts or some less-than-complete assemblage of the components parts may be provided for final assembly at some point prior to its use in implanting the osteochondral graft. For example, as provided to the surgeon, the plunger 40 may not already be inserted into tube 30.

Assembly of the delivery device 10 is readily straightforward and apparent to one of ordinary skill in the art having the benefit of this disclosure. In accordance with various embodiments described herein, handle 50, if not integral with tube 30, is attached to the proximal end 31 of tube 30. O-ring is placed within the annular recess 55 disposed in the inner surface of the proximal end 53 of the bore 54 of the handle 50. Spring tab assembly 90 is attached to the tube 30 such that tabs 95 reside in apertures 38. The distal tip 44 of plunger 40 is inserted into the proximal end 31 of tube 30 (initially through the proximal end of handle 50 if the handle 50 is not integral with tube 30).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. For example, while the primary intended use of the delivery device of the present invention is for use in implanting osteochondral grafts, it is envisioned that the delivery device could be used for implanting other tissue implants. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The indefinite articles "a" or "an", as used in the claims, are defined herein to mean one or more than one of the element that it introduces.

What is claimed is:

1. An implant delivery device, comprising:
 a tube including a bore;
 a plunger disposed within the bore; and
 an implant retention assembly including a collar coupled to the tube, a first element protruding into the bore through an aperture in the tube, and a second element protruding into the bore through the aperture in the tube, the first element and the second element defining portions of a tab member that extends from the collar and toward the aperture in the tube, wherein contact between the plunger and the first element displaces the second element to permit receipt or release of an implant from the bore.

2. The implant delivery device of claim 1, wherein the first element is a first protrusion extending from an inner surface of the tab member into the bore and the second element is a second protrusion extending from the inner surface of the tab member into the bore.

3. The implant delivery device of claim 2, wherein the second protrusion is located adjacent to a distal tip of the tab member.

4. The implant delivery device of claim 1, wherein the implant retention assembly is a spring tab assembly.

5. A delivery device for an implant, comprising:
a tube including a bore extending from a proximal end to a distal end of the tube, wherein an inner dimension of the bore is sufficient to accept an implant of a desired size, and at least one aperture located adjacent the distal end of the tube;
a plunger slidably disposed within the bore of the tube and including a shaft having a proximal end and a distal end; and
an implant retention assembly including a collar coupled to the tube and at least one tab, at least a portion of the at least one tab configured to be disposed within the at least one aperture of the tube, wherein the at least one tab is biased inwardly toward a center region of the bore but is capable of being displaced outwardly to receive or release the implant.

6. The delivery device of claim 5, wherein the at least one tab includes a first tab and a second tab, and wherein the at least one aperture includes a first aperture and a second aperture.

7. The delivery device of claim 6, further comprising a first inwardly facing protrusion on the first tab and a second inwardly facing protrusion on the second tab, wherein the first and second tabs are configured to be displaced outwardly to receive or release the implant when the first and second inwardly facing protrusions are contacted by the distal end of the shaft.

8. The delivery device of claim 5, wherein the collar of the retention assembly is at least partially disposed within a recess in the outer surface of the tube.

9. The delivery device of claim 5, wherein a distal tip of the at least one tab includes a retention member configured for retaining the implant within the bore of the tube.

10. The delivery device of claim 5, further comprising a pliable member positioned within the bore of the tube and configured for providing frictional engagement with the shaft of the plunger.

11. An implant delivery device, comprising:
a tube including a bore;
a plunger disposed within the bore; and
an implant retention assembly including a first element protruding into the bore through a first aperture in the tube, a second element protruding into the bore through the first aperture in the tube, a third element protruding into the bore through a second aperture in the tube, and a fourth element protruding into the bore through the second aperture in the tube, the first element and the second element defining portions of a first tab member, and the third element and the fourth element defining portions of a second tab member, wherein the first and second tab members extend from a collar coupled to the tube, and wherein movement of a shaft of the plunger within the tube causes the first and second tab members to be displaced away from each other, with contact between the plunger and the first and third elements displacing the second and fourth elements, respectively, to permit receipt of an implant from the bore.

* * * * *